United States Patent [19]

Takano et al.

[11] Patent Number: 5,504,219

[45] Date of Patent: Apr. 2, 1996

[54] OPTICALLY ACTIVE COMPOUNDS AND INTERMEDIATES THEREOF, AND PROCESS FOR MANUFACTURING SAME

[75] Inventors: Seiichi Takano; Kunio Ogasawara, both of Sendai, Japan

[73] Assignee: Asahi Denka Kogyo K.K., Tokyo, Japan

[21] Appl. No.: 243,760

[22] Filed: May 17, 1994

Related U.S. Application Data

[62] Division of Ser. No. 36,887, Mar. 25, 1993, Pat. No. 5,352,845, which is a division of Ser. No. 658,179, Feb. 20, 1991, Pat. No. 5,262,552.

[30] Foreign Application Priority Data

| Feb. 20, 1990 | [JP] | Japan | 2-39321 |
| Feb. 20, 1990 | [JP] | Japan | 2-39322 |
| Feb. 20, 1990 | [JP] | Japan | 2-39323 |

[51] Int. Cl.$^6$ .................................................. C07D 309/30
[52] U.S. Cl. ........................................ 549/292; 549/283
[58] Field of Search ................................ 549/292, 283

[56] References Cited

U.S. PATENT DOCUMENTS

| 4,113,740 | 9/1978 | Cohen et al. | 552/310 |
| 4,153,614 | 5/1979 | Barner et al. | 552/310 |
| 4,182,719 | 1/1980 | Cohen et al. | 552/310 |
| 4,201,879 | 5/1980 | Barner et al. | 568/766 |
| 4,234,490 | 11/1980 | Barner et al. | 549/450 |
| 4,424,389 | 1/1984 | Sakito | 549/407 |
| 4,433,159 | 2/1984 | Hamamura et al. | 549/411 |
| 4,985,571 | 1/1991 | Takano et al. | 549/283 |
| 5,292,898 | 3/1994 | Hammann et al. | 549/292 |

OTHER PUBLICATIONS

March, "Advanced Organic Chemistry," John Wiley & Sons, New York (1985), pp. 394, 735.
Streitwieser, Jr. et al., "Introduction to Organic Chemistry," Macmillan Publishing Co., Inc., New York (1976), pp. 239–240.

Primary Examiner—José G. Dees
Assistant Examiner—Barbara S. Frazier
Attorney, Agent, or Firm—Sherman and Shalloway

[57] ABSTRACT

An optically active (S)- or (R)-pentane compound of the general formula (11):

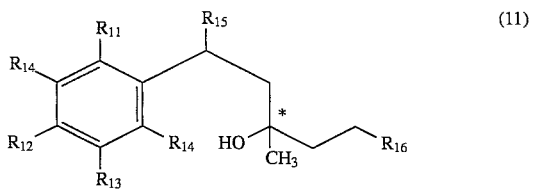

(11)

wherein $R_{11}$, $R_{12}$ and $R_{13}$ independently represent a hydrogen atom or a lower alkyl group having 1 to 4 carbon atoms, $R_{14}$ represents a hydroxy, protected hydroxy or oxo group, if $R_{14}$ is an oxo group, the ring denoting benzene in the above formula (11) is benzoquinone, $R_{15}$ represents a hydrogen atom, hydroxy or acyloxy group, $R_{16}$ represents a hydroxy or acyloxy group, and the chiral central carbon marked with a symbol * in said formula (11) alternatively has one of an R-configuration and an S-configuration, is disclosed. Further, intermediate products of the compound of the formula (11) are also disclosed. Still further, a process for manufacturing the above compounds is disclosed. The compound of the formula (11) is easily synthesized from an easily available optically active starting material.

4 Claims, No Drawings

OPTICALLY ACTIVE COMPOUNDS AND INTERMEDIATES THEREOF, AND PROCESS FOR MANUFACTURING SAME

This is a division of application Ser. No. 08/036,887, filed Mar. 25, 1993, now U.S. Pat. No. 5,352,845, which is a division of 07/658,179 filed Feb. 20, 1991, now U.S. Pat. No. 5,262,552, issued Nov. 16, 1993.

BACKGROUND OF THE INVENTION

1. Field of the Invention

The present invention relates to an optically active novel compound and intermediate products thereof, and a process for the manufacture of same.

2. Description of the Related Art

Vitamin E is a methylated derivative of a tocopherol, and includes eight kinds of naturally occurring compounds, i.e., α-, β-, γ-, and δ-tocopherols, and α-, β-, γ-, and δ-tocotrienols. Although tocopherols and tocotrienols include d-form, l-form or dl-form optical isomers, naturally occurring compounds have optical activities. Synthesized tocopherols are generally prepared in the form of a diastereomer, and it is known that a chirality of the carbon atom of the 2-position in the chroman ring has a considerable affect on the physiological activities of tocopherols.

A method of synthesizing optically active tocopherols from optically active starting materials is described in, for example, N. Cohen, et al, Journal of the American Chemical Society, 101:22, Oct. 24, 1979, 6710–6716. In the method of Cohen, et al, an optically active desired α-tocopherol is obtained by using an optically active benzopyran derivative as a starting material, to form an optically active chroman-2-methanol derivative, and then performing a Wittig coupling of the chroman derivative to form the final α-tocopherol while retaining the chirality of the starting material. In this method, however, a resolution process is required to obtain the optically active starting material, and a poisonous hydrocyanic acid must be used during the course of the synthesis process.

Further, a method of synthesizing optically active tocopherols starting from optically active phytols is described in, for example, Japanese Unexamined Patent Publications No. 59-29678 and No. 59-31726. According to the methods described in said Publications, an epoxy group is stereoselectively introduced into the 2, 3-position of the naturally occurring phytol by an enantioselective oxidation, and a reductive cleavage of the epoxy group is then performed to form a hydroxy group while retaining the chirality of the 3-position. After protecting the hydroxy group, the hydroxy group of the 1-position is oxidized to form an aldehyde group, and the obtained aldehyde group is reacted with a phenyl magnesium halide to introduce the benzene ring. A ring closure is then carried out, using the hydroxy group of the 3-position, and the desired chirality is introduced into the 2-position of the chroman ring.

In the above methods, however, many steps are required to selectively protect one of two hydroxy groups formed by the cleaving of the epoxy group. Further, because the β-oxyaldehyde intermediate is unstable, it is difficult to determine the reaction conditions. Furthermore, other disadvantages arise in that Grignard reagent, which requires anhydrous condition, and ether must be used, and complicated steps for removing the hydroxy group in the benzyl position become necessary.

Mevalonolactone is a useful compound as a starting material of various medicines, agricultural chemicals, cosmetics or food additives, or the intermediates thereof, and includes an optically active R-form (naturally occurring) compound and S-form (naturally non-occurring) compound. The naturally occurring R-form compound has the structure of the formula (35):

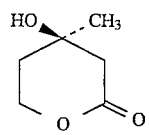
(35)

A method of synthesizing optically active mevalonolactone from optically active starting materials is described in, for example,: Japanese Unexamined Patent Publication No. 60-146840. In the method of this Patent Publication, an optically active heptenetriol derivative is prepared from an optically active oxohydroxyfuran derivative while retaining the chirality thereof, and the optically active desired mevalonolactone is then obtained through several steps from the heptenetriol derivative. In the conventional methods including the above, however, many steps are required, the chirality introducing rate is low, the procedures in the processes are difficult, and mass production is difficult.

SUMMARY OF THE INVENTION

Accordingly, an object of the present invention is to provide intermediates from which naturally occurring or non-naturally occurring tocopherols can be alternatively prepared, without the need for a resolution process and the need to use poisonous reagents, and which can be prepared from an easily available starting material having an optical activity.

A further object of the present invention is to provide a means for easily and effectively constructing the naturally occurring chirality (R), which has a considerable affect on physiological activity of tocopherol, of the carbon atom in the 2-position of the chroman ring, starting from easily available naturally occurring phytol, and synthesizing the naturally occurring α-tocopherol.

A still further object of the present invention is to provide intermediates for naturally occurring mevalonolactone, which intermediates can be prepared through a small number of steps and simple procedures, with a high chirality introducing rate, and, if necessary, by mass production.

Other objects and advantages of the present invention will be apparent from the following description.

In accordance with the present invention, there is provided an optically active (S)- or (R)-pentane compound of the general formula (11):

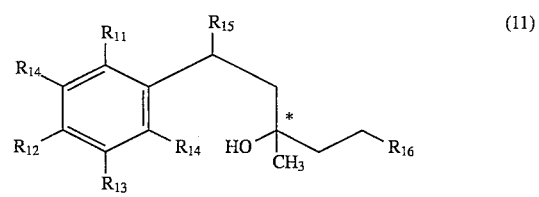
(11)

wherein $R_{11}$, $R_{12}$ and $R_{13}$ independently represent a hydrogen atom or a lower alkyl group having 1 to 4 carbon atoms, $R_{14}$ represents a hydroxy, protected hydroxy or oxo group, if $R_{14}$ is an oxo group, the ring denoting benzene in the above formula (11) is benzoquinone, $R_{15}$ represents a hydrogen atom, hydroxy or acyloxy group, $R_{16}$ represents a hydroxy or acyloxy group, and the chiral central carbon atom marked with a symbol * in said formula (11) has either an R-configuration or an S-configuration.

Further, in accordance with the present invention, there is provided an optically active compound of the general formula (21):

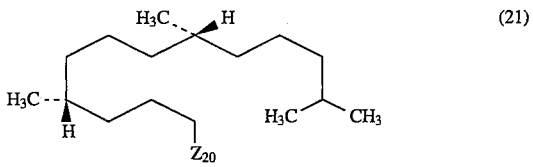

wherein (i) $Z_{20}$ represents a (1S, 2S)-1,2-epoxy-1-methyl-propyl group substituted at the 3-position with an OT group, or a halogen atom, T denotes an alkylsulfonyl group, an alkylsulfonyl group having a substituted alkyl moiety, a phenylsulfonyl group, or a phenylsulfonyl group having a substituted benzene ring, (ii) $Z_{20}$ represents a (1S)-1-hydroxy-1-methyl-propynyl-2 group, or (iii) $Z_{20}$ represents a (1S)-1-hydroxy-1-methyl-propynyl-2 group substituted at the 3-position with a phenyl group of the general formula (22):

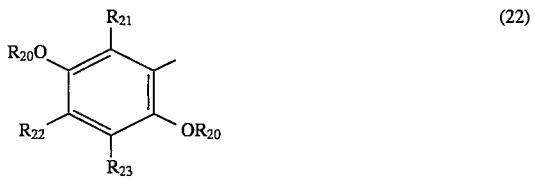

wherein $R_{21}$, $R_{22}$ and $R_{23}$ independently represent a group providing a hydrogen atom or a lower alkyl group having 1 to 4 carbon atoms, and $R_{20}$ represents a protected hydroxy group.

Still further, in accordance with the present invention, there is provided an optically active valerolactone compound of the general formula (31):

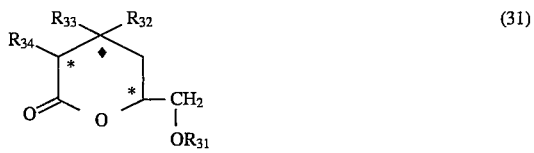

wherein $R_{31}$ represents a hydrogen atom or a group for protecting a hydroxy group, $R_{32}$ represents a lower alkyl group having 1 to 4 carbon atoms, a lower alkenyl group having 1 to 4 carbon atoms, a lower alkynyl group having 1 to 4 carbon atoms, or a phenyl group, $R_{33}$ is a hydroxy group, and $R_{34}$ is a hydrogen atom, or $R_{33}$ and $R_{34}$ together form an epoxy group, and the chiral central carbon atoms marked with symbols * and ♦ in said formula (31) have either an R-configuration or an S-configuration.

Still further, in accordance with the present invention, there is provided an optically active hexane compound of the general formula (32):

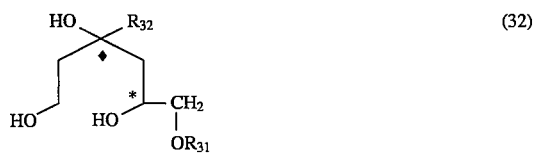

wherein $R_{31}$ represents a hydrogen atom or a group for protecting a hydroxy group, $R_{32}$ represents a lower alkyl group having 1 to 4 carbon atoms, a lower alkenyl group having 1 to 4 carbon atoms, a lower alkynyl group having 1 to 4 carbon atoms, or a phenyl group, and the chiral central carbon atoms marked with symbols * and ♦ in said formula (32) have either an R-configuration or an S-configuration.

Still further, in accordance with the present invention, there is provided an optically active hexynoate compound of the general formula (33):

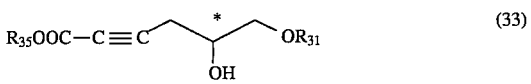

wherein $R_{31}$ represents a hydrogen atom or a group for protecting a hydroxy group, $R_{35}$ represents a hydrogen atom, an alkyl group, an alkyl group substituted with one or more phenyl groups, an alkenyl group, a phenyl group, a substituted phenyl group or a trialkylsilyl group, and the chiral central carbon atom marked with a symbol * in said formula (33) has either an R-configuration or an S-configuration.

Still further, in accordance with the present invention, there is provided an optically active unsaturated valerolactone compound of the general formula (34):

wherein $R_{31}$ represents a hydrogen atom or a group for protecting a hydroxy group, $R_{32}$ represents a lower alkyl group having 1 to 4 carbon atoms, a lower alkenyl group having 1 to 4 carbon atoms, a lower alkynyl group having 1 to 4 carbon atoms, or a phenyl group, and the chiral central carbon atom marked with a symbol * in said formula (34) has either an R-configuration or an S-configuration.

Still further, in accordance with the present invention, there is provided a process for manufacturing the above compounds.

DESCRIPTION OF THE PREFERRED EMBODIMENTS

The process for manufacturing the compound of the general formula (11) according to the present invention includes the following steps.

(a-1) A step comprising reducing an optically active (S)- or (R)-mevalonolactone of the formula (12):

wherein the symbol * has the same meaning as above to obtain an optically active corresponding (S)- or (R)-mevalonolactol of the formula (13):

wherein the symbol * has the same meaning as above.

(b-1) A step comprising reacting the lactol of the formula (13) and a benzenemagnesium halide of the general formula (14):

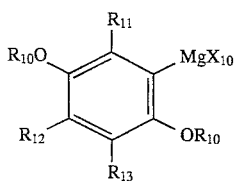

(14)

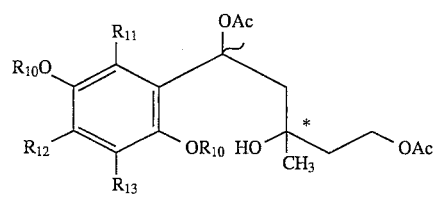

(16)

wherein $R_{10}$ represents a group for protecting a hydroxy group, preferably a lower alkyl group having 1 to 4 carbon atoms and optionally substituted with one or more lower alkyl groups having 1 to 4 carbon atoms (such as methyl, methoxymethyl or methoxyethoxymethyl), a benzyl or substituted benzyl group, a substituted phenyl group (such as p-methoxyphenyl), or a silyl group substituted with one or more lower alkyl groups having 1 to 4 carbon atoms (such as t-butyldimethylsilyl), $R_{11}$, $R_{12}$ and $R_{13}$ independently represent a hydrogen atom Or a lower alkyl group having 1 to 4 carbon atoms, preferably methyl or ethyl group, and $X_{10}$ represents a halogen atom, preferably bromine or iodine atom, to thereby obtain an optically active corresponding (S)- or (R)-phenylpentanetriol compound [hereinafter optionally referred to as phenyltriol compound] of the general formula (15):

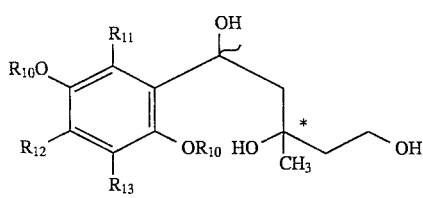

(15)

wherein $R_{10}$, $R_{11}$, $R_{12}$, $R_{13}$ and the symbol * have the same meaning as above, while retaining the S-configuration or R-configuration alternatively possessed by the chiral central carbon atom *. In the phenyltriol compound (15) obtained in this step, a configuration of another chiral central carbon atom in the benzyl position is not necessarily one of the above alternatives but may be in the form of an SR mixture.

(a'-1) A step comprising obtaining the phenyltriol compound (15) from the mevalonolactone (12) by one step, instead of the above steps (a-1) and (b-1): A step comprising reducing the optically active (S)- or (R)-mevalonolactone of the formula (12) to obtain the optically corresponding (S)- or (R)-mevalonolactol of the formula (13) and, without isolating the resulting product, adding to the same reaction vessel the prepared benzene magnesium halide of the general formula (14), to thereby carry out the reaction therebetween and obtain the optically active corresponding (S)- or (R)-phenylpentanetriol compound of the General formula (15) while retaining the S-configuration or R-configuration alternatively possessed by the chiral central carbon atom *. In the phenyltriol compound (15) obtained in this step, a configuration of another chiral central carbon atom in the benzyl position is not necessarily one of the above alternatives but may be in the form of an SR mixture.

(c-1) A step comprising acylating the phenyltriol compound (15), to thereby obtain an optically active corresponding (S)- or (R)-phenylpentanediester compound [hereinafter optionally referred to as diester compound] of a formula (16):

wherein Ac represents an acyl group, preferably an acyl group derived from an aliphatic or aromatic carboxylic acid, for example, acetyl, propionyl, butyryl, valeryl or benzoyl, $R_{11}$, $R_{12}$, $R_{13}$, $R_{10}$ and the symbol * have the same meanings as above, while retaining the S-configuration or R-configuration alternatively possessed by the chiral central carbon atom *. in the diester compound (16) obtained in this step, a configuration of another chiral central carbon atom in the benzyl position is not necessarily one of the above alternatives but may be in the form of an SR mixture.

(d-1) A step comprising reducing the diester compound (16), to thereby obtain an optically active corresponding phenylpentanediol compound [hereinafter optionally referred to as phenyldiol compound] of a formula (17):

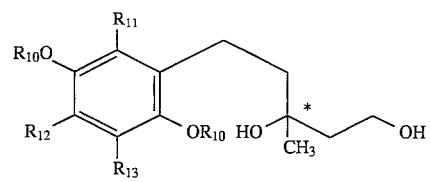

(17)

wherein $R_{11}$, $R_{12}$, $R_{13}$, $R_{10}$ and the symbol * have the same meanings as above, while retaining the S-configuration or R-configuration alternatively possessed by the chiral central carbon atom *.

(e-1) A step comprising removing the protecting group $R_{10}$ from the phenyldiol compound (17), to thereby obtain an optically active corresponding (S)- or (R)-benzoquinonepentanediol compound [hereinafter optionally referred to as benzoquinonediol compound] of the formula (18):

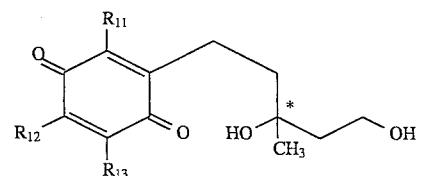

(18)

wherein $R_{11}$, $R_{12}$, $R_{13}$ and the symbol * have the same meanings as above, while retaining the S-configuration or R-configuration alternatively possessed by the chiral central carbon atom *.

(f-1) A step comprising catalytically reducing the benzoquinonediol compound (18), to thereby obtain an optically active corresponding (S)- or (R)-hydroquinonepentanediol compound [hereinafter optionally referred to as hydroquinonediol compound] of the general formula (19):

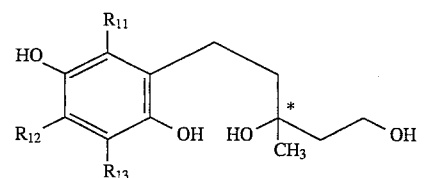

(19)

wherein $R_{11}$, $R_{12}$, $R_{13}$ and the symbol * have the same meanings as above, while retaining the S-configuration or R-configuration alternatively possessed by the chiral central carbon atom *.

(g-1) A step comprising treating the hydroquinonediol compound (19) under hydrogenolysis conditions, to thereby obtain an optically active corresponding (S)- or (R)-chroman-2-ethanol compound [hereinafter optionally referred to as chromanethanol compound] of the general formula (110):

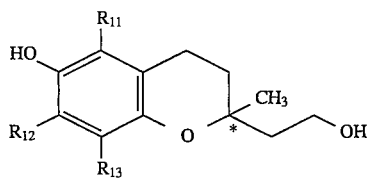
(110)

wherein $R_{11}$, $R_{12}$, $R_{13}$ and the symbol * have the same meanings as above, while retaining the S-configuration or R-configuration alternatively possessed by the chiral central carbon atom *.

The process for manufacturing the compound of the general formula (21) according to the present invention includes the following steps.

(a-2) A step comprising sulfonylating, particularly tosylating, a hydroxy group at 1-position of an optically active phytol epoxide of the formula (23):

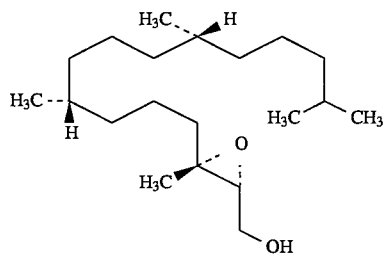
(23)

to obtain an optically active corresponding sulfonic acid ester of the general formula (21a):

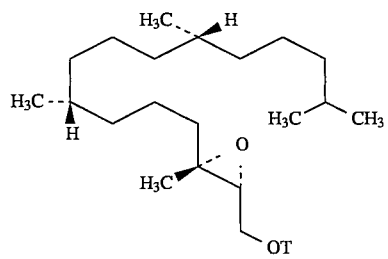
(21a)

wherein T represents an alkylsulfonyl group, preferably a lower alkylsulfonyl group such as a methylsulfonyl group; an alkylsulfonyl group having a substituted alkyl moiety, preferably a halogenated lower alkylsulfonyl group such as a trichloromethylsulfonyl, trifluoromethylsulfonyl or phenylsulfonyl group; a phenylsulfonyl group having a substituted benzene ring, preferably a phenylsulfonyl group having a benzene ring substituted with one or more lower alkyl groups or halogen atoms such as a tosyl p-bromophenylsulfonyl or p-nitrophenylsulfonyl group, while retaining the chirality.

(b-2) A step comprising treating the sulfonic acid ester of the formula (21a) with a halogenating agent to thereby obtain an optically active corresponding halogenated compound of the general formula (21b):

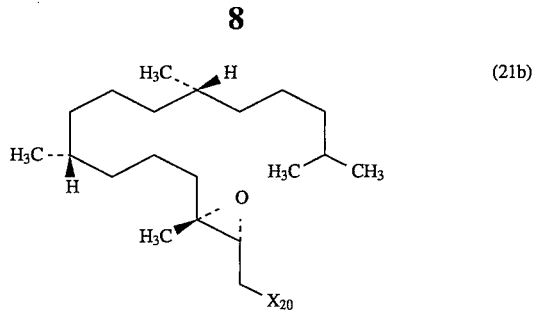
(21b)

wherein $X_{20}$ represents a halogen atom, preferably a chlorine, bromine or iodine atom, while retaining the chirality.

(c-2) A step comprising treating the halogenated compound of the general formula (21b) with a strong base, to thereby obtain an optically active corresponding acetylene alcohol compound of the formula (21c):

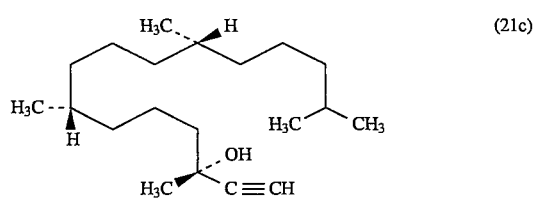
(21c)

while retaining the chirality. (d-2) A step comprising reacting the acetylene alcohol of the formula (21c) with a benzene halide of the general formula (24):

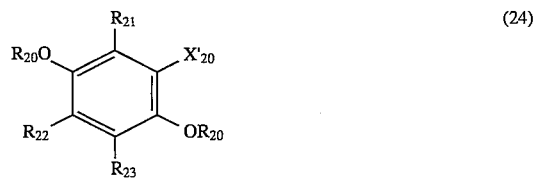
(24)

wherein $R_{20}$ represents a group for protecting a hydroxy group, preferably a lower alkyl group having 1 to 4 carbon atoms and optionally substituted with one or more lower alkyl groups having 1 to 4 carbon atoms (such as methyl, methoxymethyl or methoxyethoxymethyl), a benzyl or substituted benzyl group, is substituted phenyl group (such as p-methoxyphenyl), or a silyl group substituted with one or more lower alkyl groups having 1 to 4 carbon atoms (such as t-butyldimethylsilyl), $R_{21}$, $R_{22}$ and $R_{23}$ independently represent a hydrogen atom or a lower alkyl group having 1 to 4 carbon atoms, preferably methyl or ethyl group, and $X'_{20}$ represents a halogen atom, preferably bromine or iodine atom, to thereby obtain an optically active corresponding phenylacetylene compound [hereinafter optionally referred to as phenylacetylene compound] of the general formula (21d):

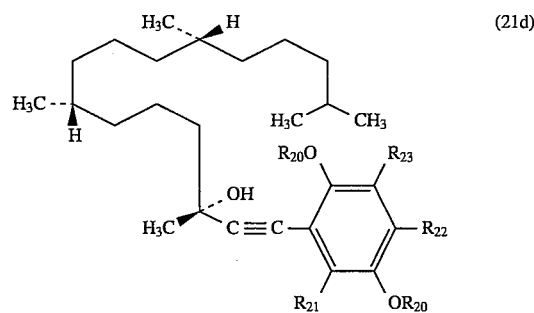
(21d)

wherein $R_{21}$, $R_{22}$, $R_{23}$ and $R_{20}$ have the same meanings as above, while retaining the chilarity.

(e-2) A step comprising reducing the phenylacetylene compound (21d), to thereby obtain an optically active corresponding saturated compound of the general formula (25):

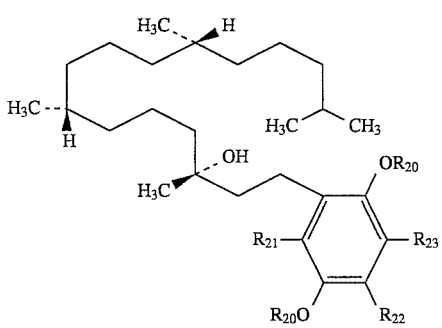
(25)

wherein $R_{21}$, $R_{22}$, $R_{23}$ and $R_{20}$ have the same meanings as above, while retaining the chirality.

The process for manufacturing the compound of the general formula (31) according to the present invention includes the following steps.

(a-3) A step comprising reacting an optically active (S)- or (R)-glycidol compound of the general formula (36):

(36)

wherein $R_{31}$ represents a hydrogen atom, or a group for protecting a hydroxy group, preferably a lower alkyl group having 1 to 4 carbon atoms and optionally substituted with one or more lower alkoxy groups having 1 to 4 carbon atoms (such as methyl, methoxymethyl or methoxyethoxymethyl), a benzyl or substituted benzyl group, a substituted phenyl group (such as p-methoxyphenyl), or a silyl group substituted with one or more lower alkoxy groups having 1 to 4 carbon atoms (such as t-butyldimethylsilyl), and the chiral central carbon atom marked with a symbol * in said formula (36) has either an R-configuration or an S-configuration, with a propargylic acid of the general formula (37):

$$HC \equiv C-COOR_{35} \quad (37)$$

wherein $R_{35}$ represents a hydrogen atom; an alkyl group, preferably a lower alkyl group, such as methyl or ethyl group; an alkyl group substituted with a phenyl group, preferably a lower alkyl group having 1 to 4 carbon atoms substituted with one or more phenyl groups, such as a benzyl group; an alkenyl group, preferably a lower alkenyl group having 1 to 4 carbon atoms, such as an allyl group; a phenyl group; a substituted phenyl group, preferably a phenyl group substituted with one or more lower alkyl or alkoxy groups having 1 to 4 carbon atoms, such as p-methoxy group; or a trialkylsilyl group, such as trimethylsilyl group, or a derivative thereof, to thereby obtain an optically active corresponding (S)- or (R)-hexynoate compound of the general formula (33):

(33)

wherein $R_{31}$, $R_{35}$ and the symbol * have the same meanings as above, while retaining the S-configuration or R-configuration alternatively possessed by the chiral central carbon atom *.

(b-3) A step comprising reacting the hexynoate compound of the general formula (33) and a nucleophilic agent of the general formula (38):

$$M^I M^{II}(R_{32})_2 \quad (38)$$

wherein $M^I$ represents a univalent metallic ion, such as lithium or copper, $M^{II}$ represents a divalent metallic ion, such as copper or magnesium, $R_{32}$ represents a lower alkyl group having 1 to 4 carbon atoms, preferably methyl or ethyl group; a lower alkenyl group having 1 to 4 carbon atoms, preferably vinyl group; a lower alkynyl group having 1 to 4 carbon atoms, preferably ethynyl group; or phenyl group, to thereby obtain an optically active corresponding (S)- or (R)-unsaturated valerolactone compound of the general formula (34):

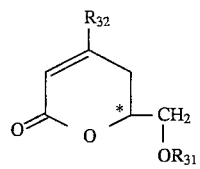
(34)

wherein $R_{31}$, $R_{32}$ and the symbol * have the same meanings as above, while retaining the S-configuration or R-configuration alternatively possessed by the chiral central carbon atom *.

(c-3) A step comprising oxidizing the unsaturated valerolactone compound (34), to thereby obtain an optically active corresponding (S)- or (R)-epoxyvalerolactone compound of the general formula (31a):

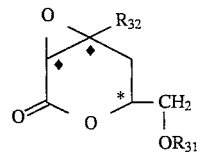
(31a)

wherein $R_{31}$, $R_{32}$ and the symbols * and ♦ have the same meanings as above, while retaining the S-configuration or R-configuration alternatively possessed by the chiral central carbon atom *. In the epoxyvalerolactone compound (31a) obtained in this step, other chiral central carbon atoms ♦ bonded with the ethoxy group, independently, may have either an R-configuration or an S-configuration, respectively.

(d-3) A step comprising reducing the epoxyvalerolactone compound (31a), to thereby obtain an optically active corresponding protected hydroxyvalerolactone compound of the general formula (31b):

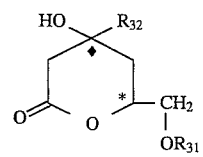
(31b)

wherein $R_{31}$, $R_{32}$, and the symbols * and ♦ have the same meanings as above, while retaining the S-configuration or R-configuration alternatively possessed by the chiral central carbon atoms * and ♦.

(e-3) A step comprising removing the protecting group $R_{31}$ from the protected hydroxyvalerolactone compound (31b), to thereby obtain an optically active corresponding free (S)- or (R)-hydroxyvalerolactone compound of the general formula (31c):

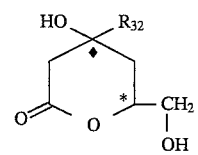
(31c)

wherein $R_{32}$ and the symbols * and ♦ have the same meanings as above, while retaining the S-configuration or R-configuration alternatively possessed by the chiral central carbon atoms * and ♦.

(f-3) A step comprising performing alkaline hydrolysis of the free hydroxyvalerolactone compound (31c) in the same reaction vessel, to cleave the glycol moiety therein, then reducing the resulting aldehyde group, and thereafter, rendering the reaction mixture acidic to thereby obtain an (S)-mevalolactone of the formula (39):

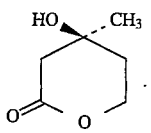
(39)

(g-3) A step comprising reducing the protected hydroxyvalerolactone compound (31b), to thereby obtain an optically active corresponding (S)- or (R)-hexane compound of the general formula (32):

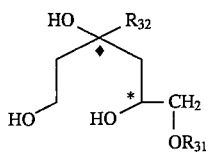
(32)

wherein $R_{31}$, $R_{32}$, and the symbols * and ♦ have the same meanings as above, while retaining the S-configuration or R-configuration alternatively possessed by the chiral central carbon atoms * and ♦.

(h-3) A step comprising performing debenzylation of the (S)- or (R)-hexane compound (32), and alkaline hydrolysis in the same reaction vessel to cleave the glycol moiety therein, then reducing the resulting aldehyde group, and thereafter, rendering the reaction mixture acidic to thereby obtain an (R)-mevalolactone of the formula (35):

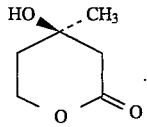
(35)

The steps (a-1) to (g-1) will be described hereinafter in detail.

Step (a-1)

The starting mevalonolactone (12) contains a chiral center, and thus includes an S-form and an R-form. Each of mevalonolactones (12) in the S-form and the R-form may be prepared by the known process described in, for example, Japanese Unexamined Patent Publication No. 60-146840. When mevalonolactone (12) in the S-form or the R-form is reduced with a metal hydride reducing agent, preferably an aluminum hydride reducing agent, more preferably a dialkyl aluminum hydride (such as dibutyl aluminum hydride, or trialkoxy lithium aluminum hydride), in an atmosphere of an inert gas (such as an argon or nitrogen gas) and at a low temperature (such as 0° C. to –78° C., preferably –10° C. to –78° C.), in an anhydrous aprotic solvents(such as tetrahydrofuran, toluene, hexane or ether), the desired mevalonolactol (13) is obtained as a waxy solid, while retaining an unchanged chirality, in a substantially pure form which may be used in a subsequent step without purification.

Step (b-1)

The optically active mevalonolactol (13) obtained in the above step (a-1) is gradually added at a low temperature of about 0° C. to –20° C. to the magnesium halide compound (14) previously prepared in an organic solvent (for example, ether, tetrahydrofuran or dioxane) in an atmosphere of an inert gas (such as an argon or nitrogen gas). After a reaction at about 0° C. to a room temperature is completed, the phenyltriol compound (15) is obtained as an oil while retaining the chirality stemming from the mevalonolactol (13). The pentane chain of the phenyltriol compound (15) includes 2 chiral central carbon atoms, i.e., (a) the chiral central carbon atom stemming from the starting mevalonolactol compound (13), and (b) a chiral central carbon atom which is newly formed by the reaction of the mevalonolactol (13) and the magnesium halide compound (14) and which is in the benzyl position. The configuration of the former chiral central carbon atom (a) is maintained in the step (b-1). The configuration of the latter chiral central carbon atom (b) is not an alternative but may be in the form of an epimer mixture of about 1:1.

The resulting compound may be used in the subsequent step, after purification (for example, by silica gel column chromatography) if necessary.

Step (a'-1)

In this step (a'-1), the starting mevalonolactone (12) in the S-form or the R-form is reduced to form the mevalonolactol (13) while retaining an unchanged chirality.

Subsequently, to the same reaction vessel containing the mevalonolactol (13) without purification, the magnesium halide compound (14) previously prepared in an organic solvent (for example, ether, tetrahydrofuran or dioxane) is gradually added at about 0° C., and after the reaction is performed therein at a room temperature, the phenyltriol compound (15) is obtained as an oil while retaining the chirality. The phenyltriol compound (15) is a compound which is the same as the product of the above step (b-1), and thus the pentane chain thereof also includes 2 chiral central carbon atoms. The configuration of the chiral central carbon atom (a) stemming from the starting mevalonolactol compound (13) is retained in the step (a'-1). Nevertheless, the configuration of the chiral central carbon atom (b) newly formed by the reaction of the mevalonolactol (13) and the magnesium halide compound (14) is not an alternative but may be in the form of an epimer mixture of about 1:1.

The resulting compound may be used in the subsequent step, after purification (for example, by silica gel column chromatography) if necessary.

Step (c-1)

As the acylating agent, an anhydride or halide of carboxylic acid, preferably an aliphatic or aromatic carboxylic acid, for example, acetic acid, propionic acid, butyric acid, isobutylic acid, valeric acid, isovaleric acid, or benzoic acid may be used. The acylation may be carried out in an atmosphere of an inert gas (such as an argon or nitrogen gas), at an atmospheric temperature, in an organic solvent, such as dichloromethane, ether, tetrahydrofuran or dioxane, in the presence of an amine, for example, a tertiary amine such as trialkyl amine, dimethylaminopyridine or an inorganic salt such as sodium hydrogencarbonate.

The hydroxy groups at the 1- and 5-positions in the phenyltriol (15) are acylated in this step (c-1). The hydroxy group in the 3-position, however, is not acylated, but remains free.

The configurations of two chiral central carbon atoms in the pentane chain are retained, and the resulting compound may be used in the subsequent step, after purification (for example, by silica gel column chromatography) if necessary.

Step (d-1)

When the diester compound (16) is reduced in a nonaqueous liquid (for example, liquid ammonia, or a lower alkyl primary amine such as methyl amine or ethyl amine) at a low temperature (for example, –40° C. to –20° C.) with an alkali metal (for example, metallic lithium or sodium), the acyloxy group at the 1-position is substituted with a hydrogen atom, and acyloxy group at the 5-position is substituted with a hydroxy group. Alternatively, the acyl group at the 1-position may be hydrogenolyzed by a catalytic hydrogenation in the presence of palladium carbon.

Although the chiral center in the pentane chain disappears after the above reduction, the configuration of the chiral central carbon atom at the 3-position [stemming from mevalonolactone (12)] is retained. The resulting compound may be used in the subsequent step, after purification (for example, silica gel column chromatography), if necessary.
Step (e-1)

The benzoquinonediol compound (18) may be obtained as an oil, while retaining the chirality, by removing the protecting group $R_{10}$ with an oxidizing agent [for example, salt of cerium (IV), preferably ammonium cerium nitrate] in an atmosphere of an inert gas (such as an argon or nitrogen gas), at an atmospheric temperature, in an aqueous-organic solvent, preferably hydrous acetonitrile, hydrous tetrahydrofuran or hydrous dioxane. The configuration of the chiral center in the pentane chain of the benzoquinonediol compound (18) is retained.

The resulting compound may be used in the subsequent step, after purification (for example, silica gel column chromatography), if necessary.
Step (f-1)

The hydroquinonepentanediol compound (19) may be obtained as an oil, while retaining the chirality, by reducing the benzoquinonediol compound (18) in a hydrogen stream with or without pressure, at an atmospheric temperature, in the presence of a catalytic reducing agent, for example, platinum or palladium. The resulting hydroquinonepentanediol compound (19) is very labile, and therefore, can be used in the subsequent step without purification.
Step (g-1)

The hydroquinonepentanediol compound (19) is refluxed in a nonpolar organic solvent (for example, benzene, toluene, or cyclohexane) in the presence of an alkyl or phenylsulfonic acid (for example, p-toluenesulfonic acid) to cause an intramolecular dehydrocondensation, and then cyclization, whereby the chroman ethanol compound (110) is obtained while retaining the chirality. Accordingly, the configuration of the chiral central carbon atom stemming from the starting mevalonolactone (12) is introduced into the 2-position of the chroman ring. The purification is carried out by silica gel column chromatography.

The chroman ethanol compound (110) in the form of a racemic modification is known, but the optically active compounds of the S-form and R-form can not be obtained unless a resolution procedure is used. The tocopherol having a naturally occurring form (i.e., R-form), which may be prepared from the chroman ethanol compound (110), exhibits a far greater physiological activity than that having the S-form.

An optically active tocopherol compound can be prepared from the optically active chroman ethanol compound (110), while retaining the chilarity of the starting chroman ethanol compound (110), by effecting a benzylation of the phenolic hydroxy group in the chroman ethanol compound (110), then a tosylation of an active hydroxy group, and thereafter, a coupling of Grignard reagent to the tosylated side chain to introduce a side chain of tocopherol, and finally, a removal of the benzyl group on the phenolic hydroxy group.

According to the steps (a-1) to (g-1) of the present invention, novel intermediates are provided which may be prepared from an easily available mevalonolactone having an optical activity and from Which tocopherols having either a naturally occurring or non-occurring configuration can be alternatively synthesized. The intermediate compounds are useful as an intermediate for various antioxidizing agents. Further, the intermediate compounds can be easily and safely prepared, because neither a resolution procedure nor poisonous reagents are required in the process for the manufacture thereof.

The steps (a-2) to (e-2) will be described hereinafter in detail.
Step (a-2)

The starting phytol epoxide of the general formula (23) may be prepared by a known enantio-oxidation of a naturally occurring phytol (26) of the formula (26):

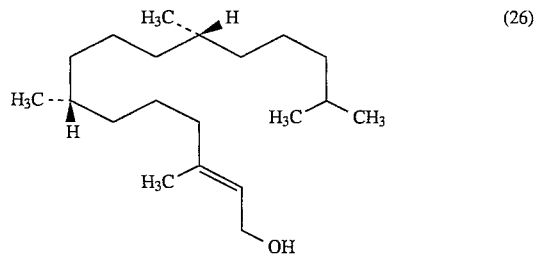

The phytol epoxide (23) may be converted to the sulfonic acid ester (21a) by a reaction with sulfonic acid or a derivative thereof in an atmosphere of an inert gas (such as an argon or nitrogen gas) and at a low temperature (such as +5° C. to −5° C.), in an anhydrous aprotic solvent (such as dichloromethane), in the presence of a tertiary amine. The chirality of the phytol epoxide (23) is retained in the step (a-2).

The resulting compound may be used in the subsequent step, after purification (for example, by silica gel column chromatography) if necessary.
Step (b-2)

As the halogenating agent, alkali metal halide, for example, chloride, bromide or iodide of lithium, sodium or potassium may be used. Halogenation may be carried out in an atmosphere of an inert gas (such as an argon or nitrogen gas) at an elevated temperature (for example, 50° to 100° C.) in an anhydrous condition, in an aprotic solvent (for example, dimethylformamide). The chirality of the starting sulfonic acid ester (21a) is retained in the step (b-2).

The resulting compound may be used in the subsequent step, after purification (for example, by silica gel column chromatography) if necessary.
Step (c-2)

The acetylene alcohol compound (21c) may be obtained while retaining the chirality of the 3-position of the starting halide compound (21b), by treating the halide compound (21b) prepared in the above step (b-2), in an atmosphere of an inert gas (such as an argon or nitrogen gas) at a low temperature (for example, −10° to −30° C.) in an aprotic solvent (for example, tetrahydrofuran, toluene, hexane or ether) with a strong base, for example, metallic amide (such as lithium amide, lithium diisopropylamide, sodium amide or potassium amide), alkali metal alkyl or phenyl (such as butyl lithium or phenyl lithium).

The resulting compound may be used in the subsequent step, after purification (for example, by silica gel column chromatography) if necessary.
Step (d-2)

Chloride, bromide or iodide may be used as the halogenated benzene compound (24). The process of this step (d-2) may be carried out in an atmosphere of an inert gas (such as an argon or nitrogen gas) at an atmospheric or elevated temperature (for example, about 100° C.) in an anhydrous condition, in an organic solvent (for example, triethylamine, acetonitrile or dimethylsulfoxide), in the presence of a palladium catalyst, preferably under ultrasonication.

In this step (d-2), the phenylacetylene compound (21d) is obtained while retaining the chirality of the starting acetylene alcohol compound (21c).

The resulting compound may be used in the subsequent step, after purification (for example, by silica gel column chromatography) if necessary.

Step (e-2)

The reduction of the phenylacetylene compound (21d) may be carried out by passing hydrogen stream (1 to 5 atmospheric pressure) in the presence of a catalyst (for example, palladium oxide, palladium-carbon or Raney nickel), in an alcoholic solvent, at an atmospheric temperature. When the olefin compound is obtained, the reduction thereof is carried out under the same conditions as mentioned above.

In this step (e-2), the saturated compound (25) is obtained while retaining the chirality of the starting phenyl acetylene compound (21d).

The resulting compound may be used in the subsequent step, after purification (for example, by silica gel column chromatography) if necessary.

The optically active saturated compound (25) may be converted to the naturally occurring tocopherol (2R-form), by a known process. When the saturated compound (25) is treated in an atmosphere of an inert gas (such as an argon or nitrogen gas), at an atmospheric temperature, in an aqueous-organic solvent, preferably hydrous acetonitrile, hydrous tetrahydrofuran or hydrous dioxane with an oxidizing agent [for example, salt of cerium (IV), preferably ammonium cerium nitrate], an optically active corresponding benzoquinone compound of the general formula (27):

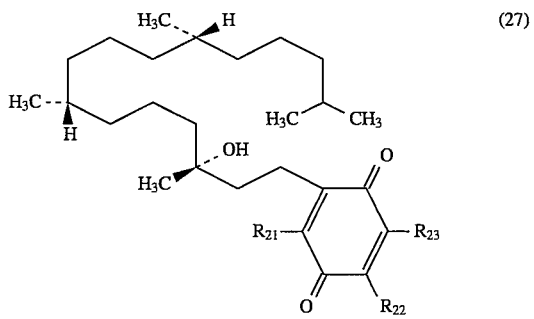

wherein $R_{21}$, $R_{22}$ and $R_{23}$ have the same meanings as above, while retaining the chirality.

Thereafter, when the benzoquinone compound (27) is reduced in a hydrogen stream with or without pressure, in the presence of a reducing catalyst (such as platinum or palladium), an optically active corresponding hydroquinone compound of the general formula (28):

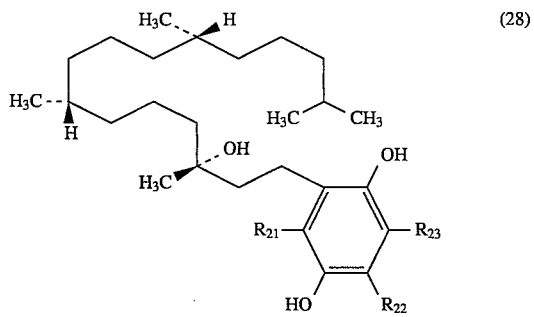

wherein $R_{21}$, $R_{22}$ and $R_{23}$ have the same meanings as above, can be obtained while retaining the chirality. The naturally occurring α-tocopherol may be obtained while retaining the chilarity by cyclizing the resulting hydroquinone compound (28) by known methods.

As shown above, the naturally occurring α-tocopherol can be prepared by simple, procedures while retaining the chirality stemming from the naturally occurring phytol.

According to the steps (a-2) to (e-2) of the present invention, an efficient process is provided whereby the naturally occurring chirality can be easily constructed, starting from easily available naturally occurring phytol.

The steps (a-3) to (h-3) will be described hereinafter in detail.

Step (a-3)

The starting glycidol (36) contains a chiral center, and thus includes an S-form and an R-form. Each of the glycidols in the S-form and the R-form is known.

The reaction of the glycidol (36) and the propargylic acid (37) or the derivative thereof may be carried out in an atmosphere of an inert gas (such as an argon or nitrogen gas) and at a low temperature (for example, 0° C. to −120° C., preferably −10° C. to −100° C.), in an aprotic solvent (such as tetrahydrofuran, toluene, hexane or ether) in the presence of a strong base (for example, alkyl lithium) or Lewis acid catalyst (for example, boron trifluoride, preferably boron trifluoride ether). In this step, the configuration of the chiral central carbon atom stemming from the starting glycidol (36) is introduced into the hexynoate compound (33). The resulting compound may be purified by silica gel column chromatography Step (b-3)

This step is carried in out in an atmosphere of an inert gas (such as an argon or nitrogen gas) at a low temperature (for example, 0° C. to −100° C., preferably −10° C. to −80° C.) in an aprotic solvent (such as tetrahydrofuran, toluene, hexane or ether) in the presence of a copper (I) compound (such as CuI or CuCN). As the nucleophilic agent, lithium dialkyl cuprate, lithium diphenyl cuprate, or alkyl or phenyl magnesium halide may be used.

The configuration of the 5-position chiral central carbon atom of the hexynoate compound (33) is retained and introduced into the unsaturated valerolactone compound (34). The resulting compound may be used in the subsequent step, after purification (for example, by silica gel column chromatography) if necessary.

Step (c-3)

The epoxidation of the unsaturated valerolactone may be carried out in an atmosphere of an inert gas (such as an argon or nitrogen gas) at an atmospheric temperature in a polar organic solvent (such as lower alcohol or hydrous lower alcohol) in the presence of alkali hydroxide (such as sodium hydroxide or potassium hydroxide), using hydroperoxide (such as hydroperoxide, t-butyl hydroperoxide).

In this epoxidation, the configuration of the 5-position chiral central carbon atom of the valerolactone ring is not changed and is retained. Further, new chiral centers are introduced into the 2, 3-positions. The kind of configuration of the 2, 3-positions depends on the configuration of the 5-position chiral central carbon atom of the unsaturated valerolactone compound (34). More particularly, the epoxidation occurs in the anti-side selectively against the 5-position substituent. When the configuration of the 5-position chiral central carbon atom of the unsaturated valerolactone compound (34) is the S-form, the 2-position is an R-form and the 3-position is an R-form. Further, when the configuration of the 5-position chiral central carbon atom of the unsaturated valerolactone compound (34) is the R-form, the 2-position is an S-form and the 3-position is an S-form.

The resulting compound may be used in the subsequent step, after purification (for example, by silica gel column chromatography) if necessary.

Step (d-3)

The reduction of the epoxy group may be carried out in an atmosphere of an inert gas (such as an argon or nitrogen gas), at an atmospheric temperature, in an alcoholic solvent, such as lower alcohol or hydrous lower alcohol, in the presence of a lower carboxylic acid (such as acetic acid), using diphenyl diselenide, phenyl diselenide, phenylselenyl halide, sodium boron hydride or potassium boron hydride.

The resulting compound may be used in the subsequent step, after purification (for example, by silica gel column chromatography) if necessary.

The reduction causes a disappearance of the chiral center at the 2-position of the valerolactone ring, but the configurations of two chiral central carbon atoms at the 3- and 5-positions are retained.

Each of S-mevalolactone or R-mevalolactone can be prepared from the valerolactone compound (31b) obtained in this step (d-3). More particularly, when the steps (e-3) and (f-3) are carried out after the step (d-3), the 3S-mevaloloactone can be prepared, and when the steps (g-3) and (h-3) are carried out after the step (d-3), the 3R-mevalolactone can be prepared. The configuration of the final mevalolactone is dependent only upon the steps to be selected, not upon the starting material used and the configuration of the mevalolactone (31b).

Step (e-3)

The protecting group $R_{31}$ can be removed by a passing hydrogen stream (1 to 5 atmospheric pressure) in the presence of a reducing catalyst (such as palladium-carbon, or palladium hydroxide) in an alcoholic solvent in an atmospheric temperature.

In this step (e-3), the configurations of two chiral central carbon atoms at the 3- and 5-positions in the valerolactone ring are retained.

The resulting compound may be used in the subsequent step, after purification for example, silica gel column chromatography), if necessary.

Step (f-3)

The alkaline hydrolysis of the free hydroxyvalerolactone compound (31c) may be carried out, using a dilute aqueous liquid of an alkali metal hydroxide (such as sodium hydroxide or potassium hydroxide) in an aprotic solvent (for example, tetrahydrofuran, toluene, hexane or ether) at an atmospheric temperature. After the reaction mixture is rendered weakly alkaline (pH=about 8 to 7) by adding a weak acid (for example, carbon dioxide gas) at a low temperature (for example, 0° C. to a room temperature), the glycol moiety is cleaved by adding an aqueous periodate (for example, sodium periodate) solution. Shortly after the cleaving, the reaction mixture is reduced in the same vessel by a reducing agent (for example, sodium boron hydride). After the reaction is completed, the reaction solution is made acidic by an inorganic acid (for example, sulfuric acid).

The steps (e-3) and (f-3) may be performed in the same vessel.

The resulting compound may be purified (for example, by silica gel column chromatography) if necessary, to produce pure (S)-mevalolactone.

Step (g-3)

The hydroxyvalerolactone (31b) prepared in the step (d-3) may be reduced in an atmosphere of an inert gas (such as an argon or nitrogen gas), at a low temperature (for example +10° C. to −10° C.) in an aprotic solvent (for example, tetrahydrofuran, toluene, dioxane or ether) in the presence of a hydride reducing agent (such as lithium aluminum hydride, diisobutyl aluminum hydride, or boron potassium hydride).

In this step (g-3), the configurations of two chiral central carbon atoms at the 3- and 5-positions in the valerolactone ring are retained.

The resulting compound may be used in the subsequent step, after purification (for example, by silica gel column chromatography), if necessary.

Step (h-3)

The protecting group $R_{31}$ can be removed by passing a hydrogen stream (1 to 5 atmospheric pressure) in the presence of a reducing catalyst (such as palladium-carbon, or palladium hydroxide) in an alcoholic solvent in an atmospheric temperature. Then, a 1,2-glycol moiety is oxidatively cleaved at a low temperature (for example, +10° C. to −10° C.) by periodate (such as sodium periodate). After the disappearance of the starting material is affirmed, and further an oxidizing agent (such as chromium oxide or Jones reagent) is added to exhaust the starting material, the reaction solution is made acidic by an inorganic acid (for example, sulfuric acid).

The steps (e-3) and (f-3) may be performed in the same vessel, and (R)-mevalactene may be thus obtained.

The resulting compound may be purified (for example, by silica gel column chromatography, if necessary.

The resulting (S)- or (R)-mevalolactone may be used as an intermediate for synthesizing medicines. Further, (S)- or (R)-mevalolactone may be converted to (S)- or (R)-mevalonic acid and used as an agent for facilitating the growth of animals, plants or microorganisms.

According to steps (a-3) to (h-3) of the present invention, each of two antipodes of mevalolactone can be prepared from an easily available starting material having an optical activity, the procedures are simple and suitable for mass production, and the introducing rate of the chiral center is high. Further, a desired compound can be obtained while retaining the chilarity of the starting material, without racemization.

EXAMPLES

The present invention now will be further illustrated by, but is by no means limited to, the following Examples.

Example 1

Preparation of 2ξ-hydroxy-(4R)-mevlonolactol

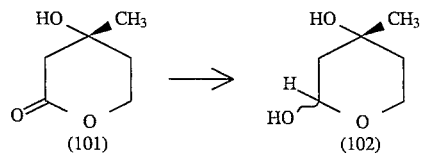

In an atmosphere of an argon stream, a toluene solution (1.5 ml:2.7 mmol) of 1.8M diisobutylaluminum hydride was gradually added at −30° C. to a tetrahydrofuran solution (4 ml) containing 211 mg (1.62 mmol) of (R)–(+)-mevalonolactone (101). The reaction mixture was stirred at −30° C. for 45 minutes, quenched with 10% aqueous sodium hydroxide solution, stirred again at a room temperature for 1 hour, and then filtered with celite. Thereafter, the solvent was evaporated from the resulting filtrate to obtain an oily product. Further, the above celite used for the filtration was extracted overnight with ethyl acetate to obtain an oily product. These oily products were combined and treated with silica gel column chromatography, and from the ethyl acetate effluent, 180 mg (85%) of the above-mentioned compound (102) was obtained as a colorless oil.

Mass analysis (m/e): 132 (M+), 68 (100%).
IR (neat) cm$^{-1}$: 3300.
$^1$H-NMR (CDCl$_3$) δ: 4.9–5.39 (1H, m) 4.4–3.5 (2H, m) 4.6 and 3.25 (2H, brd and brd), 2.0–1.4 (4H, m), 1.3, 1.25 (3H, s×2).

EXAMPLE 2

Preparation of (3R)-1-(2,5-dimethoxy-3,4,6-trimethylphenyl)-3-methyl-pentane-1ξ,3,5-triol (102) ⟶ (103)

In an atmosphere of an argon stream, 1.1 g (0.045 mol) of magnesium, one drop of methyl iodide, and a catalytic amount of iodine were added to 30 ml of tetrahydrofuran, and further, a solution of 10.4 g (0.04 mol) of 2,5-dimethoxy-3,4,6-trimethyl-bromobenzene in 15 ml of tetrahydrofuran was added dropwise over 40 minutes while refluxing the tetrahydrofuran. The reaction was completed by refluxing for further 30 minutes, to thereby form 2,5-dimethoxy-3,4,6-trimethylbenzene magnesium bromide. Then, after cooling to 0° C., 580 mg (4.4 mmol) of the lactol compound (102) prepared in Example 1 was added and stirred at a room temperature for 2 hours, an aqueous sodium bicarbonate saturated solution was added to the reaction mixture, and an extraction with diethyl ether was carried out. The organic phase was washed with an aqueous sodium chloride saturated solution, and dried over anhydrous magnesium sulfate, the solvent was evaporated under a reduced pressure, and the residue was treated by silica gel column chromatography. Then, 1.35 g (98.5%) of the above-mentioned compound (103) was obtained from the ethyl acetate effluent as a colorless oil.

Mass analysis (m/e): 312 (M$^+$), 209 (100%)
IR (neat) cm$^{-1}$: 3370
$^1$H-NMR (CDCl$_3$) δ: 5.45 (2H, m), 4.90 (2H, m), 4.25–3.60 (8H, m), 2.4–2.1 (9H, m), 1.85–1.5 (4H, m), 1.5 and 3.2 (3H, s×2).

EXAMPLE 3

Preparation of (3S)-1-(2,5-dimethoxy-3,4,6-trimethylphenyl)-3-methyl-pentane-1ξ,3,5-triol (101)→(103)

In an atmosphere of i an argon stream, 0.9 ml (0.9 mmol) of a solution of 1.0M diisobutyl aluminum hydride in dichloromethane was gradually added at −30° C. to 3 ml of a solution of 89 mg (0.68 mmol) of (R)-(+)-mevalonolactone (101) in tetrahydrofuran, and the reaction mixture was stirred at −30° C. for 20 minutes. After the temperature of the reaction mixture was raised to 0° C., a solution of a Grignard reagent (prepared in a different vessel as mentioned below) in tetrahydrofuran was added, and then, the whole was stirred at a room temperature for 3 hours. To the resulting reaction solution, aqueous concentrated ammonium hydroxide solution was added, and the reaction mixture was stirred for 2 hours. The reaction solution was filtered with celite. After adding diethyl ether, the reaction solution was washed with a brine and dried over anhydrous magnesium sulfate, the solvent was evaporated under a reduced pressure, and the residue was treated by silica gel column chromatography. Then, 180 mg (80%) of the above-mentioned compound (103) was obtained from the ethyl acetate effluent as a colorless oil.

The results of a mass analysis, IR and NMR were identical to those in Example 2.

The Grignard reagent used in Example 3 was prepared by adding 114 mg (7 mmol) of magnesium, one drop of methyl iodide and one piece of iodine to 8 ml of tetrahydrofuran in an atmosphere of an argon stream, and adding dropwise 1.6 g (6.15 mmol) of 2,5-dimethyl-3,4,6-trimethylbromobenzene over 40 minutes while refluxing tetrahydrofuran.

EXAMPLE 4

Preparation of (3S)-1-(2,5-dimethoxy-3,4,6-trimethylphenyl)-3-methyl-pentane-1ξ,3,5-diacetoxy-3-ol (103) ⟶ (104)

In an atmosphere of an argon stream, 1.3 g (4.167 mmol) of the triol compound (103) prepared in Example 3 was dissolved in 15 ml of dichloromethane, and then 1.89 ml (0.02 mmol) of acetic anhydride, 3.48 ml (0.025 mmol) of triethylamine and 50 mg of dimethylaminopyridine were added, and the whole was stirred at a room temperature for 1 hour. Then, the reaction solution was diluted with 40 ml of dichloromethane, washed successively with an aqueous sodium bicarbonate saturated solution and an aqueous sodium chloride saturated solution, and then dried over anhydrous magnesium sulfate. The solvent was evaporated under a reduced pressure. The residue was treated by silica gel column chromatography, and 1.55 g (92%) of the above-mentioned compound (104) was obtained from the ether/hexane (1:1) effluent as a colorless oil.

Mass analysis (m/e): 396 (M$^+$), 206 (100%).
IR (neat) cm$^{-1}$: 3450, 1720.
$^1$H-NMR (CDCl$_3$) δ: 6.50 (1H, m), 4.20 (2H, m), 3.80 (3H, s), 3.65 (3H, s), 2.38 (3H, s), 2.18 (6H, s), 2.10 (3H, s), 2.05 (3H, s×2), 2.5–1.2 (5H, m), 1.29 and 1.20 (3H, s×2).

EXAMPLE 5

Preparation of (S)-1-(2,5-dimethoxy-3,4,6-trimethylphenyl)-3-methyl-pentane-3,5-diol (104) ⟶ (105)

Diacetyloxy compound (104) (132 mg; 0.33 mmol) prepared in Example 4 was dissolved in 3 ml of tetrahydrofuran, and 15 ml of aqueous ammonia was added at −33° C. to the solution. Lithium (20 mg ;2.86 mmol) was then gradually added while stirring at the same temperature, and 10 minutes later, ammonium chloride was added. After evaporating ammonia, diethyl ether was added. The resulting mixture was washed with an aqueous sodium bicarbonate saturated solution and an aqueous sodium chloride saturated solution, and then dried over anhydrous magnesium sulfate. The solvent was evaporated under a reduced pressure, and the residue was treated by silica gel column chromatography. Then, 75 mg (76%) of the above-mentioned compound (105) was obtained from the effluent of ether/hexane (2:3) as a colorless oil.

Mass analysis (m/e): 296 (M⁺), 193 (100%).
$[\alpha]_D^{25}$=+3.80 (c=1.504, CHCl₃)
IR (neat) cm⁻¹: 3350.
¹H-NMR (CDCl₃) δ: 3.93 (2H, t, J=7 Hz), 3.70 (3H, s), 3.65 (3H, s), 2.60 (4H, m), 2.26 (3H, s), 2.18 (6H, s), 1.33 (3H, s).

EXAMPLE 6

Preparation of (S)-1-(2,5-dioxo-3,4,6-trimethylcyclohexadiene-1,4)-3-methyl-pentane-3,5-diol

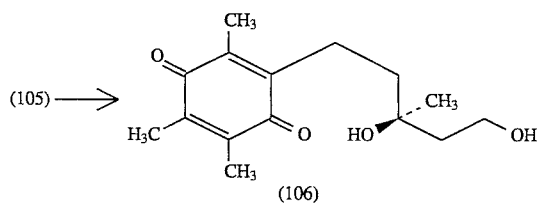

To a solution of 650 mg (2.196 mmol) of the diol compound (105) prepared in Example 5 in 20 ml of acetonitrile and 20 ml of H₂O, 297 g (8.78 mmol) of ammonium cerium (IV) nitrate was added in an atmosphere of an argon stream at a room temperature. After stirring for 10 minutes, diethyl ether and an aqueous sodium bicarbonate saturated solution were added. The diethyl ether layer was washed with a brine, and dried over an anhydrous magnesium sulfate. The solvent was evaporated under a reduced pressure, and the residue was treated by silica gel column chromatography. Then, 471 mg (81%) of the above-mentioned compound (106) was obtained from the ether/hexane (5:1) effluent as a yellow oil.

$[\alpha]_D^{27}$=+6.33° (c=1.116, CHCl₃).
Mass analysis (m/e): 266 (M⁺), 178 (100%).
IR (neat) cm⁻¹: 3350, 1650.
¹H-NMR (CDCl₃) δ: 3.95 (2H, t, J=7 Hz), 2.58 (4H, m), 2.05 (3H, s), 2.00 (6H, s), 1.9–1.45 (4H, m), 1.33 (3H, s).

EXAMPLE 7

Preparation of (S)-1-(2,5-dihydroxy-3,4,6-trimethylphenyl)-3-methyl-pentane-3,5-diol and (S)-(−)-6-hydroxy-2,5,7,8-tetramethylchroman-2-ethanol

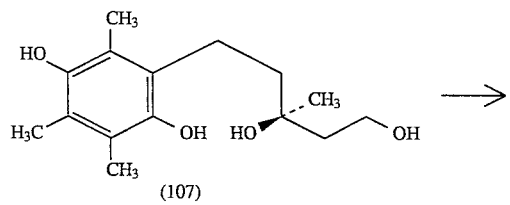

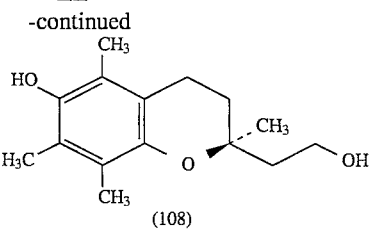

To a solution of 471 mg (1.77 mmol) of the benzoquinone compound (106) prepared in Example 6 in 7 ml of ethyl acetate, 50 mg of 10% palladium on carbon was added, and the whole was stirred in an atmosphere of a hydrogen stream at a room temperature for 2 hours. The reaction solution was filtered with celite. The solvent was evaporated under a reduced pressure to thereby obtain a very labile hydroxyphenyl compound (107).

To the residue containing the hydroxyphenyl compound (107), 15 ml of benzene and 20 mg of p-toluene sulfonic acid were added. The reaction mixture was heated under reflux for 1 hour, cooled to a room temperature, diluted with diethyl ether, washed successively with an aqueous sodium bicarbonate saturated solution and an aqueous sodium chloride saturated solution, and then dried over anhydrous magnesium sulfate. The solvent was evaporated under a reduced pressure and the residue was treated by silica gel column chromatography. From the effluent of ether/hexane (1:1), 310 mg (71%) of the above-mentioned chroman compound (108) was obtained as a colorless crystal.

Mass analysis (m/e): 250 (M⁺), 164 (100%).
IR (neat) cm⁻¹: 3400.
¹H-NMR (CDCl₃) δ: 4.7 (1H, brs), 3.90 (2H, t, J=7 Hz), 2.66 (2H, t, J=7 Hz), 2.16 (3H, s), 2.10 (6H, s), 1.7–2.2 (4H, m), 1.28 (3H, s).
Melting point: 137°–138° C.

EXAMPLE 8

(a) Preparation of (2S, 3S)-epoxy-(3S, 7R, 11R)-3,7,11,15-tetramethylhexadecane-1-ol Naturally occurring phytol (26)

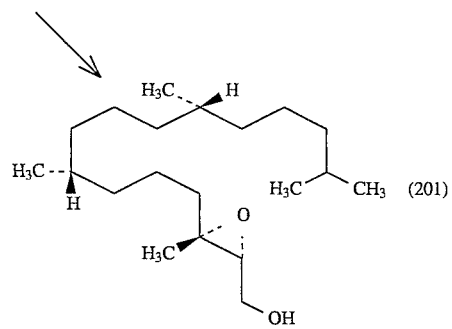

In an atmosphere of an argon stream and at −30° C., 1.45 ml (6.90 mmol) of D-(−)-diisopropyl tartrate and 2.05 ml (6.89 mmol) of titanium tetraisopropoxide were added to a suspension of 2.38 g of 4A molecular sieves in 20 ml of dichloromethane. After the reaction mixture was allowed to stand for 7 minutes, a solution (5.60 ml; 9.86 mmol) of t-butylperoxide (1.76 mol) in dichloromethane was added, and the whole was stirred at the same temperature for 105 minutes. Then, a solution of 2.01 g (6.77 mmol) of phytol, i.e., (3S, 7R, 11R)-1-hydroxy-3,7,11,15-tetramethyl-2-hexadecene (26) in 40 ml of dichloromethane, was added dropwise over 10 minutes, and the whole was stirred for 16 hours under the same conditions. Then, 6.0 ml of an aqueous 3N-$K_2CO_3$ solution was added, and the reaction mixture was heated to a room temperature. Further, 4.0 g of celite was added 1 hour later, and the whole was stirred for 15 minutes. Then, the celite was filtered off, the filtrate was concentrated under a reduced pressure, diethyl ether and $H_2O$ were added, and the organic layer was taken. The aqueous layer was extracted with diethyl ether. The resulting extract and the above organic layer were combined together, washed with an aqueous sodium chloride solution and dried over magnesium sulfate. Thereafter, the solvent was evaporated under a reduced pressure to obtain 3.52 g of a crude product as a light yellow oil. The crude product was treated by column chromatography wherein 80 g of silica gel was used, and 2.00 g (yield: 95%) of the above-mentioned epoxide compound (201) was obtained as a colorless oil from the diethyl ether/n-hexane (1:4, v/v) effluent.

$[\alpha]_D^{26}=+4.44°$ (c=0.99, $CHCl_3$).

$[\alpha]_D^{28}=+4.88°$ (c=2.80, ethyl alcohol).

IR $\nu_{max}$ (neat) $cm^{-1}$: 3430, 1460, 1380, 1030, 865.

H-NMR ($CDCl_3$, $\delta$): 0.70–1.83 (37H, m, 1H exchangeable), 2.96 (1H, dd, J=6.1 Hz, 4.6 Hz), 3.45–4.03 (2H, m), Sharp peaks: 0.83, 0.88, 0.90, 1.60.

C-NMR ($CDCl_3$, $\delta$): 16.74 (q), 19.64 (q), 19.75 (q), 22.55 (t), 22.64 (q), 22.73 (q), 24.48 (t), 24.80 (t), 27.98 (d), 32.75 (d), 32.79 (d), 36.96 (t), 37.30 (t), 37.34 (t), 37.43 (t), 38.84 (t), 39.38 (t), 61.39 (t), 61.47 (s), 63.20 (d).

MS m/z: 312 ($M^+$), 294, 281, 250, 97, 71, 57 (100%).

High-MS m/z ($M^+$): Calculated ($C_{20}H_{40}O_2$): 312.3028 Found: 312.3053

The physicochemical data of the naturally occurring phytol used in Example 8 are as follows:

$[\alpha]_D^{29}=-1.35°$ (c=1.00, $CHCl_3$).

IR $\nu_{max}$ (neat) $cm^{-1}$: 3340, 1460, 1375, 1000.

H-NMR ($CDCl_3$, $\delta$): 0.70–1.80 (35H, m, 1H $D_2O$ exchangeable with $D_2O$), 1.85–2.15 (2H, m), 4.00–4.30 (2H, m), 5.23–5.57 (1H, m).

Sharp peaks: 0.83, 0.88, 0.90, 1.57, 1.68.

[4.00–4.30 (2H, m) is converted to 4.14 (2H, brd, J=6.8 Hz) by $D_2O$ substitution.]

C-NMR ($CDCl_3$, $\delta$): 16.14 (q), 19.72 (q), 19.75 (q), 22.63 (q), 22.73 (q), 24.50 (t), 24.82 (t), 25.18 (t), 27.98 (d), 32.71 (d), 32.80 (d), 36.73 (t), 37.32 (t), 37.40 (t), 37.46 (t), 39.39 (t), 39.91 (t), 59.16 (t), 123.34 (d), 139.63 (s) .

MS m/z: 297 ($M^++1$), 296($M^+$), 278, 196, 123, 71 (100%), 57.

High-MS m/z ($M^+$): Calculated ($C_{20}H_{40}O$ ): 296.3079 Found: 296.3078

(b) Preparation of (2S, 3S)-epoxy-(3S, 7R, 11R)-3,7,11,15-tetramethyl-1-tosyloxy-hexadecane

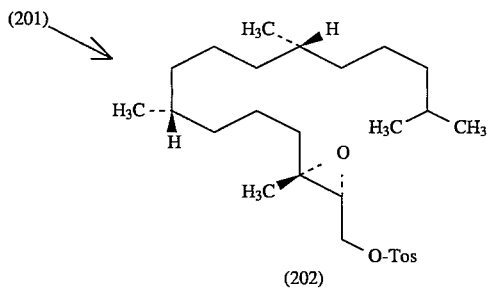

(202)

wherein Tos represents a tosyl group.

To a solution of 492 mg (1.57 mmol) of the phytol epoxide compound (201) prepared in Example 1 (a) in 10 ml of dichloromethane, 0.55 ml (3.95 mmol) of triethylamine and 19.0 mg (0. 156 mmol) of 4 -dimethylaminopyridine, and then 370 mg (1.94 mmol) of p-toluenesulfonylchloride were added in an atmosphere of an argon stream under anhydrous conditions while cooling with an ice. After allowing to stand for 5 minutes, the reaction solution was heated to a room temperature, and stirred for 12 hours. After adding 10 ml of dichloromethane, the whole was successively washed with 5% HCl aqueous solution, an aqueous sodium bicarbonate saturated solution and an aqueous sodium chloride saturated solution, and dried over anhydrous magnesium sulfate. The solvent was evaporated under a reduced pressure to thereby obtain 1.00 g of a crude product as a light yellow oil.

The crude product was treated by column chromatography wherein 25 g of silica gel was used, and 720 mg (yield: 99%) of the above-mentioned tosylated compound (102) was obtained from the diethyl ether/n-hexane (1:15, v/v) effluent as a colorless oil.

$[\alpha]_D^{27}=+15.92°$ (c=1.06, $CHCl_3$).

IR $\nu_{max}$ (neat) $cm^{-1}$: 1480, 1365, 1190, 1180, 970, 770, 665.

H-NMR ($CDCl_3$, $\delta$): 0.60–1.82 (36H, m), 2.45 (3H, s), 2.96 (1H, t, J=5.6 Hz), 3.88–4.33 (2H, m), 7.35 (2H, d, J=8.4 Hz), 7.86 (2H, d, J=8.4 Hz).

Sharp peaks: 0.83, 0.88, 0.90, 1.19.

[2.96 (1H, t, J=5.6 Hz) seems to be 2.96 (1H, dd, J=5.7 Hz, 4.7 Hz), and 3.88–4.33 (2H, m) seems to be 4.12 (1H, d, J=5.7 Hz)+3.88–4.33 (1H, m).]

MS m/z: 466 ($M^+$), 448, 436, 355, 281, 97, 91, 71, 57 (100%).

High-MS m/z ($M^+$): Calculated ($C_{27}H_{46}O_4S$): 466.3117 Found: 466.3136

EXAMPLE 9

Preparation of (2S, 3S)-epoxy-(3S, 7R, 11R)-3,7,11,15-tetramethyl-1-chloro-hexadecane

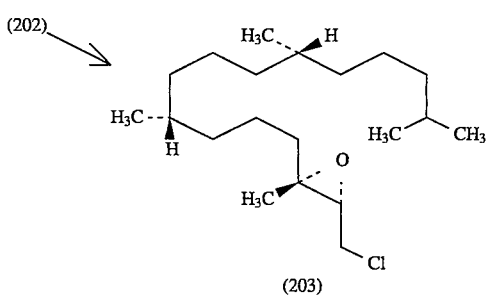

(203)

To a solution of 720 mg (1.54 mmol) of the tosylated compound (202) prepared in Example 1(b) in 10 ml of dimethylformamide, 80 mg (1.89 mmol) of lithium chloride was added, and the whole was heated at 60° C. for about 5 hours in an atmosphere of an argon stream under anhydrous conditions. The solvent was evaporated under a reduced pressure. Diethyl ether (20 ml) and $H_2O$ (10 ml) were added to the residue, and the organic layer was taken. The aqueous layer was extracted with diethyl ether and the extract and the above organic layer were combined together. The mixture was dried over a magnesium sulfate. The solvent was evaporated under a reduced pressure, and the crude product (650 mg) was obtained as a light yellow oil. The crude product was treated by column chromatography wherein 40 g of silica gel was used. From the effluent of diethyl ether/n-hexane (1:2, v/v), 497 mg (yield: 97%) of the above-mentioned chloride compound (203) was obtained as a colorless oil.

$[\alpha]_D^{30}=-9.47°$ (c=1.07, $CHCl_3$).

IR $v_{max}$ (neat) $cm^{-1}$: 1460, 1380, 910, 740.

H-NMR ($CDCl_3$, δ): 0.60–1.85 (36H, m), 3.02 (1H, t, J=6.5 Hz), 3.44 (1H, dd, J=11.2 Hz, 6.8 Hz), 3.72 (1H, dd, J=11.2 Hz, 6.1 Hz).

Sharp peaks: 0.80, 0.83, 0.88, 1.31.

[3.02 (1H, t, J=6.5 Hz) seems to be 3.02 (1H, dd, J=6.8 Hz, 6.1 Hz ).]

MS m/z: 295 ($M^+$—Cl), 281, 250, 97, 91, 71, 57 (100%).

High-MS m/z ($M^+$—Cl): Calculated ($C_{20}H_{39}O$): 295. 3001 Found: 295.3002

EXAMPLE 10

Preparation of (2S, 3S)-epoxy-(3S, 7R, 11R)-3,7,11,15-tetramethyl-1-chloro-hexadecane (201)→(203)

To a solution of 859 mg (2.75 mmol) of the epoxide compound (201) prepared in Example 1(a) in 15 ml of carbon tetrachloride, 1.09 g (4.16 mmol) of triphenylphosphine was added, and the whole was heated at 80° C. for 20 hours in an atmosphere of an argon stream under anhydrous conditions. After cooling to a room temperature, 30 ml of diethylether was added, and the whole was filtered with celite. The filtrate was washed with an aqueous sodium chloride saturated solution, and then dried over magnesium sulfate. The solvent was evaporated under a reduced pressure, and the crude product (2.78 g) was obtained as a white crystal. The crude product was treated by column chromatography wherein 50 g of silica gels was used, and 739 mg (yield: 81%) of the above-mentioned chloride compound (203) was obtained from the diethyl ether/n-hexane (1:100, v/v) effluent as a colorless oil. The physicochemical data of $[\alpha]_D^{30}$, IR, H-NMR, MS and High-MS are identical to those of Example 9.

EXAMPLE 11

Preparation of 3-hydroxy-(3S, 7R, 11R)-3,7,11,15-tetramethyl-1-hexadecyne

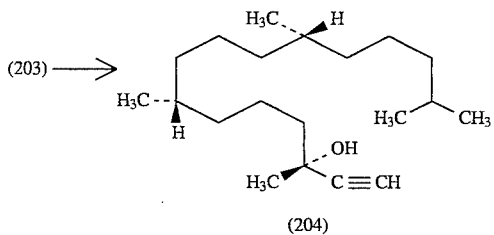

(204)

A mixture solution was prepared from 8.00 ml (11.2 mmol) of 1.40M n-butyl lithium/n-hexane, and 5.0 ml of tetrahydrofuran. To the mixture solution, a solution of 739 mg (2.23 mmol) of the chloride compound (203) prepared in Example 9 in 16 ml of tetrahydrofuran was added at –20° C. in an atmosphere of an argon stream under anhydrous conditions. An aqueous ammonium chloride saturated solution (2.0 ml) was added 20 minutes later, and then the whole was heated to a room temperature. After $H_2O$ (5.0 ml) and diethyl ether (20 ml) were added, the organic layer was taken. The aqueous layer was extracted with diethyl ether, and the extract and the above organic layer were combined together. The combined mixture was washed with an aqueous sodium chloride saturated solution, and then dried over magnesium sulfate. The solvent was evaporated under a reduced pressure, and the crude product (796 mg) was obtained as colorless liquid. The crude product was treated by column chromatography wherein 40 g of silica gel was used. From the effluent of diethyl ether/n-hexane (1:6, v/v), 624 mg (yield: 95%) of the above-mentioned acetylene alcohol compound (204) was obtained as a colorless oil.

$[\alpha]_D^{30}=+1.37°$ (c=0.73, $CHCl_3$).

IR $v_{max}$ (neat) $cm^{-1}$: 3380, 3300, 1460, 1375, 1145, 915.

H-NMR ($CDCl_3$, δ): 0.70–1.86 (36H, m), 1.94 (1H, brs, exchangeable), 2.43 (1H, s).

Sharp peaks: 0.83, 0.90, 1.50, 2.43.

MS m/z: 279 ($M^+$–15), 269, 261, 163,1 21, 95, 84, 69 (100%), 57.

High-MS m/z ($M^+$–15): Calculated ($C_{19}H_{35}O$): 279.2688 Found: 279.2661

High-MS m/z ($M^+$–25): Calculated ($C_{18}H_{37}O$): 269.2844 Found: 269. 2812.

EXAMPLE 12

Preparation of 3-hydroxy-(3S, 7R, 11R)-3,7,11,15-tetramethyl-1-(2,5-dimethoxy-3,4,6-trimethyl)phenyl-hexadecyne-1

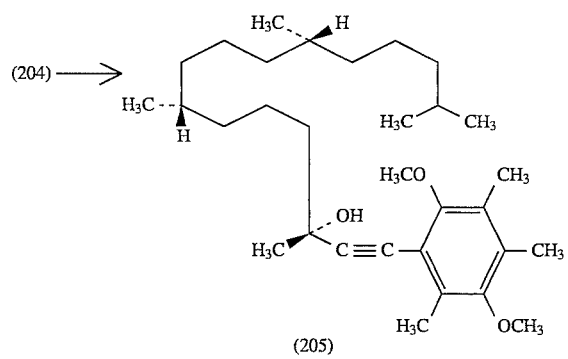

(205)

To a solution prepared by dissolving 267 mg (0.907 mmol) of the acetylene alcohol compound (204) prepared in Example 11 and 561 mg (1.83 mmol) of 2,5-dimethoxy-3, 4,6-trimethyl-benzene iodide in 5.0 ml of triethylamine, 18.6 mg (26.5 μmol) of bis(triphenylphosphine) palladium chloride and 3.2 mg (17 μmol) of copper iodide were added in an atmosphere of an argon stream under anhydrous conditions. The reaction mixture was stirred at a room temperature for 45 minutes under the irradiation the sunlight, and further subjected to the ultrasonic irradiation at 45° C. for 10 hours. After adding diethyl ether (5 ml), filtration was carried out by celite. Then, the solvent was evaporated under a reduced pressure and the residue was dissolved in diethyl ether (10 ml). The solution was successively washed with an aqueous hydrochloric acid solution (5%), an aqueous sodium bicarbonate saturated solution and an aqueous sodium chloride saturated solution, and dried over anhydrous magnesium sulfate. The solvent was evaporated under a reduced pressure, and the crude product was obtained as an orange oil. The crude product was treated by column chromatography wherein 20 g of silica gel was used. From the diethyl ether/n-hexane (1:3, v/v) effluent, 326 mg (yield: 76%) of the above-mentioned phenylacetylene compound (205) was obtained as a yellow oil. Further, 32 mg (yield: 12%) of the diacetylenediol by-product was obtained as a light yellow oil. Desired product (phenylacetylene compound):

$[\alpha]_D^{30}=+4.03°$ (c=0.73, $CHCl_3$).

IR $v_{max}$ (neat) $cm^{-1}$: 3440, 1460, 1400, 1275, 1095.

H-NMR ($CDCl_3$, δ): 0.53–2.20 (37H, m, 1H exchangeable), 2.15 (3H, s), 2.19 (3H, s), 2.33 (3H, s), 3.65 (3H, s), 3.80 (3H, s).

Sharp peaks: 0.83, 0.86, 0.89, 1.49 (exchangeable), 1.62.

MS m/z: 473 (M$^+$+15), 472 (M$^+$), 454, 441, 368, 299, 271, 249, 247 (100%), 205, 173, 149, 135, 109, 95, 83, 69, 57.

High-MS m/z (M$^+$): Calculated ($C_{31}H_{52}O_3$): 472. 3916 Found: 472. 3914

By-product (diacetylenediol):

IR $v_{max}$ (neat) cm$^{-1}$: 3340, 1460, 1375, 1145.

H-NMR (CDCl$_3$, δ): 0.65–1.83 (72H, m), 2.01 (2H, brs, exchangeable) .

Sharp peaks: 0.83, 0.90, 1.50.

MS m/z: 586 (M$^+$), 568 (M$^+$–18), 385, 361, 343, 250, 161, 147, 93, 71, 57(100%).

High-MS m/z (M$^+$): Calculated ($C_{40}H_{74}O_2$): 586.5689 Found: 586.5683.

High-MS m/z (M$^+$–18): Calculated ($C_{40}H_{72}O$): 568.5583 Found: 568.5551.

The iodide used in Example 12 was prepared by the following method:

To a solution of 2.88 g (16.0 mmol) of 1,4-dimethoxy-2, 3,5-trimethylbenzene in concentrated sulfuric acid (0.48 ml)/H$_2$O (3.50 ml)/acetic acid (16.0 ml), 2.11 g (8.31 mmol) of iodine and 1.11 g (4.87 mmol) of periodic acid [HIO$_4$.2H$_2$O] were added, and the whole was stirred at a room temperature in an atmosphere of an argon stream for 24 hours. The solvent was evaporated under a reduced pressure. The residue was dissolved in diethyl ether (20 ml) and H$_2$O (20 ml), and the organic layer was taken. The aqueous layer was extracted with diethyl ether (20 ml), and the extract and the above organic layer were combined together. The combined mixture was washed with an aqueous sodium bicarbonate saturated solution and an aqueous sodium thiosulfate solution (5%), and then dried over magnesium sulfate. The solvent was evaporated under a reduced pressure, and the crude product (3.99 g) was obtained as a light yellow semisolid oil. The crude product was treated by column chromatography wherein 80 g of silica gel was used. The desired iodide compound (3.67 g; 12.0 mmol; yield= 75%) was obtained as white columnar crystals, by recrystallizing the effluent of diethyl ether/n-hexane (1:100, v/v) from diethylether/n-hexane.

EXAMPLE 13

Preparation of 3-hydroxy-(3S, 7R, 11R)-3,7,11,15-tetramethyl-1-(2,5-dimethoxy-3,4,6-trimethyl)phenyl-hexadecane

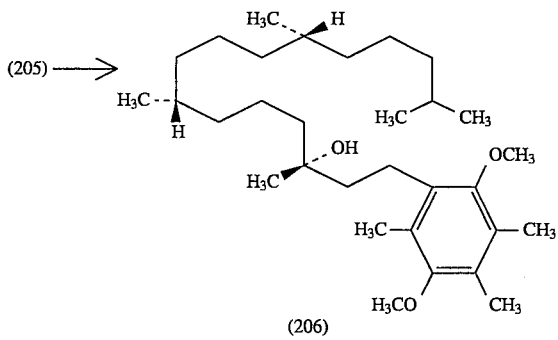

To a solution of 42.0 mg (88.8 μmol) of the phenylacetylene compound (205) prepared in Example 12 in 2.5 ml of methyl alcohol, 5.2 mg of platinum (IV) oxide was added in an atmosphere of a hydrogen stream, and the whole was stirred at a room temperature for 15 hours. The reaction solution was filtered with celite. The solvent was evaporated under a reduced pressure. The residue was treated by column chromatography wherein 6.0 g of silica gel was used. From the diethyl ether/n-hexane (1:9, v/v) effluent, 24.0 mg (57%) of the olefin compound as a colorless oil and 18.0 mg (42%) of the above-mentioned saturated compound (206) as a colorless oil were obtained.

To a solution of 24.0 mg (50.5 μmol) of the olefin compound in 1.0 ml of methyl alcohol, 2.6 mg of platinum (IV) oxide was added in an atmosphere of a hydrogen stream, and the whole was stirred at a room temperature for 41 hours. The reaction solution was filtered with celite. The solvent was evaporated under a reduced pressure. The residue was treated by column chromatography wherein 5.0 g of silica gel was used. From the effluent of diethyl ether/n-hexane (1:9, v/v), 24.0 mg (100%) of the above-mentioned saturated compound (206) was obtained as a colorless oil. The total yield was 99%.

Desired product (saturated compound):

$[α]_D^{32}$=+1.64° (c=0.72, CHCl$_3$).

IR $v_{max}$ (neat) cm$^{-1}$: 3350, 1460, 1400, 1375, 1245, 1085.

H-NMR (CDCl$_3$, δ): 0.70–1.78 (39H, m, 1H exchangeable), 2.17 (9H, s), 2.22 (9H, s), 2.53–2.72 (2H, m), 3.64 (6H, s), 3.69 (6H, s).

Sharp peaks: 0.83, 0.89, 1.24, 1.62 (1H, brs, 1H exchangeable).

MS m/z: 477 (M$^+$+1), 476 (M$^+$, 100%), 458, 251, 193.

High-MS m/z (M$^+$): Calculated ($C_{31}H_{56}O_3$): 476.4229 Found: 476.4204

Intermediate product (cis-olefin):

$[α]_D^{31}$=–30.87° (c=0.40, CHCl$_3$).

IR $v_{max}$ (neat) cm$^{-1}$: 3480, 1460, 1380, 1245, 1085.

H-NMR (CDCl$_3$, δ): 0.70–1.80 (36H, m), 2.15 (9H, s), 2.17 (9H, s), 3.63 (6H, s), 3.64 (6H, s), 3.70–4.10 (1H, br, exchangeable), 5.77 (1H, br, J=12.4 Hz), 6.16 (1H, d, J=12.4 Hz).

Sharp peaks: 0.83, 0.87, 0.90, 1.58.

MS m/z: 475 (M$^+$+1), 474 (M$^+$), 250, 249 (100%), 231, 207, 193.

High-MS m/z (M$^+$): Calculated ($C_{31}H_{54}O_3$): 474.4073 Found: 474.4065

EXAMPLE 14

Preparation of 3-hydroxy-(3S, 7R, 11R)-3,7,11,15-tetramethyl-1-(2,5-dimethoxy-3,4,6-trimethyl)phenyl-hexadecane To a solution of 41.0 mg (86.9 μmol) of the phenylacetylene compound (205) prepared in Example 12 in 1.5 ml of methyl alcohol, 3.8 mg of platinum (IV) oxide was added, and the whole was stirred in an atmosphere of a hydrogen stream at a room temperature for 7 days. The reaction solution was filtered with celite. The solvent was evaporated under a reduced pressure. The residue was treated by column chromatography wherein 7.0 g of silica gel was used. From the diethyl ether/n-hexane (1:10, v/v) effluent, 38.0 mg (79.8 μmol; 92%) of the above-mentioned saturated compound (206) was obtained as a colorless oil. The physicochemical data was identical to those of Example 13.

EXAMPLE 15

Preparation of 3-hydroxy-(3S, 7R, 11R)-3,7,11,15-tetramethyl-1-(2,5-dioxy-3,4,6-trimethyl)benzoquinone-hexadecane (206) → 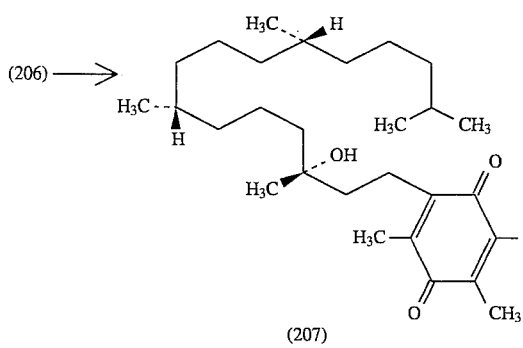

(207)

To a solution prepared by dissolving 42.0 mg (88.1 µmol) of the saturated compound (206) prepared in Example 13 in acetonitrile (1.0 ml)/H₂O (1.0 ml), 148 mg (270 µmol) of ammonium cerium (IV) nitrate [(NH₄)₂Ce(NO₃)₆] was added in an atmosphere of an argon stream at a room temperature while stirring, and the whole was stirred for further 2 hours. After the dilution was carried out by adding diethyl ether (2.0 ml) and H₂O (1.0 ml), the organic layer was taken. The aqueous layer was extracted with diethyl ether, and the extract and the above organic layer were combined together. The combined mixture was washed with an aqueous sodium chloride solution, and then dried over magnesium sulfate. The solvent was evaporated under a reduced pressure, and the crude product (44.0 mg) was obtained as an orange oil. The crude product was treated by column chromatography wherein 6.0 g of silica gel was used. From the effluent of diethyl ether/n-hexane (1:10, v/v), 24.0 mg (yield: 57%) of the olefin compound as an orange oil and 22.0 mg (yield: 56%) of the above-mentioned quinone compound (207) as a colorless oil Were obtained.

[α]$_D^{30}$=+2.45° (c=0.53, CHCl₃).

IR ν$_{max}$ (neat) cm⁻¹: 3480, 1645, 1460, 1375, 1280.

H-NMR (CDCl₃, δ): 0.64–2.38 (48H, m, 1H exchangeable), 2.38–2.82 (2H, m).

Sharp peaks: 0.83, 0.90, 1.23, 1.25, 2.01, 2.04. [1.59 (brs) is exchangeable.]

EXAMPLE 16

Preparation of 3-hydroxy-(3S, 7R, 11R)-3,7,11,15-tetramethyl-1-(2,5-dihydroxy-3,4,6-trimethyl)phenyl-hexadecane (207) → 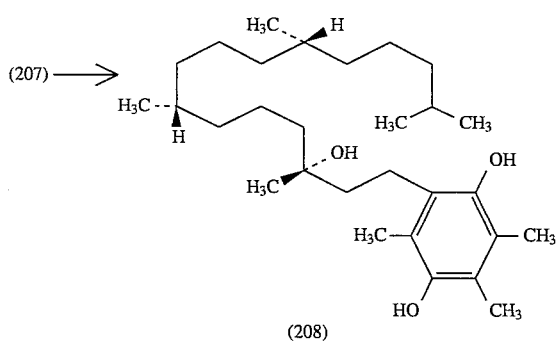

(208)

To a solution of 64.0 mg (0.143 mmol) of the quinone compound (207) prepared in Example 15 in 1.5 ml of methyl alcohol, 6.4 mg of 10% palladium on carbon was added, and the whole was stirred in an atmosphere of a hydrogen stream at a room temperature for 3 hours. The filtration was carried out with celite. The solvent was evaporated under a reduced pressure, and 65 mg of the above-mentioned crude compound (209) was obtained as a light yellow oil. The crude product was used in the next step without purification.

EXAMPLE 17

Preparation of (2R, 4'R, 8'R)-α-tocopherol (208) → 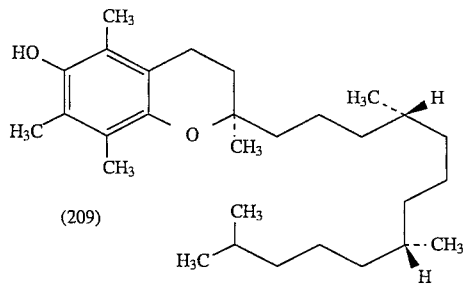

(209)

To a solution of 65 mg of the hydroquinone compound (208) prepared in Example 16 in 2.0 ml of benzene, 4.0 mg (21 µmol) of p-toluenesulfonic acid was added, and the whole was heated in an atmosphere of an argon stream for 30 minutes under reflux. After cooling, the dilution was carried out by adding diethyl ether (4 ml). The organic layer was washed successively with an aqueous sodium bicarbonate saturated solution and an aqueous sodium chloride saturated solution, and dried over anhydrous magnesium sulfate. The solvent was evaporated under a reduced pressure, and the crude product (64 mg) was obtained as a light yellow oil. The crude product was treated by column chromatography wherein 6.0 g of silica gel was used. From the effluent of diethyl ether/n-hexane (1:20, v/v), the above-mentioned tocopherol compound (209) (40.7 mg: 94.7 µmol: 66% by two steps) was obtained as a colorless oil.

[α]$_D^{30}$=−3.29° (c=0.79, benzene).

IR ν$_{max}$ (neat) cm⁻¹: 3480, 1460, 1380, 1260, 1085.

H-NMR (CDCl₃, δ): 0.65–1.93 (36H, m), 1.78 (2H, brt, J=6.8 Hz), 2.11 (6H, s), 2.16 (3H, s), 2.60 (2H, brt, J=6.8 Hz), 4.16 (1H, brs, exchangeable).

Sharp peaks: 0.83, 0.90, 1.22.

MS m/z: 431 (M⁺+1), 430 (M⁺, 100%), 207, 165.

High-MS m/z (M⁺): Calculated (C₂₉H₅₀O₂): 430.3811 Found: 430.3800.

EXAMPLE 18

Preparation of (R)-methyl-6-benzyloxy-5-hydroxy-2-hexynoate

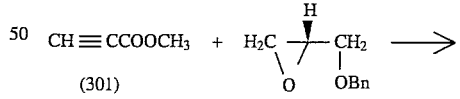

(301)  (302)

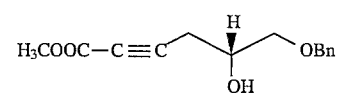

(303)

wherein Bn represents a benzyl group.

To a solution of 2.50 ml (28.1 mmol) of methyl propargylate (301) in 70 ml of tetrahydrofuran, 18.0 ml (28.0 mmol) of a solution of n-butyllithium (1.56 mol) in n-hexane was added dropwise at −90° C. over 40 minutes. Thereafter, the reaction mixture was stirred for 20 minutes. Further, a solution of 3.55 g (21.6 mmol) of (S)-O-benzylglycidol (302) in 20 ml of tetrahydrofuran was added by a cannula at the same temperature, and the whole was stirred for 5 minutes. To the resulting yellow-brown solution, 3.50 ml (28.0 mmol) of boron trifluoride-diethyl ether was added dropwise over 10 minutes, and the whole was stirred at the same temperature for 1 hour.

To the resulting reaction solution, 20 ml of an aqueous ammonium chloride saturated solution was added, and the whole was heated to a room temperature, and then extracted with 200 ml of diethyl ether. The organic layer was washed with 20 ml of an aqueous sodium bicarbonate saturated solution and then 20 ml of an aqueous sodium chloride saturated solution, and dried over magnesium sulfate. The solvent was evaporated under a reduced pressure.

The residue was treated by column chromatography wherein 200 g of silica gel was used. From the effluent of diethyl ether/n-hexane (1:1), 4.50 g (yield: 84%) of the above-mentioned 2-hexynoate compound (303) was obtained.

$[\alpha]_D^{29}=-14.7°$ (c=1.07, CHCl$_3$).
Boiling point: 160°–165° C. (0.3 mmHg) (Kugelrohl)
$^1$H-NMR (CDCl$_3$, δ): 2.60 (2H, d, J=6.0 Hz), 2.60 (1H, brs, disappeared with D$_2$O), 3.40–3.75 (2H, m), 3.78 (3H, s), 3.90–4.10 (1H, m), 4.58 (2H, s), 7.3 (5H, s).
IR ν$_{max}$ (neat) cm$^{-1}$: 3330 (br), 2260, 1710.
MS m/e: 248 (M$^+$), 91 (100%).
Elementary analysis: Calculated (C$_{14}$H$_{16}$O$_4$): C=67.71, H=6.50 Found: C=67.66, H=6.76.

EXAMPLE 19

Preparation of (R)-6-benzyloxymethyl-4-methyl-5,6-dihydro-2H-pyran-2-one

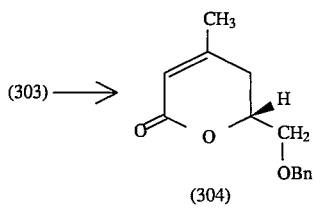

In an atmosphere of an argon stream, 8.5 mg (42.27 mmol) of copper iodide was suspended in 150 ml of tetrahydrofuran. To the suspension, 79.8 ml (84.54 mmol) of a solution of methyllithium (1.06 mol) in ether was added at 0° C., and the whole was stirred at the same temperature for 10 minutes After the reaction solution was cooled to –60° C., a solution of 4.5 g (18.1 mmol) of the hexynoate (303) prepared in Example 18 in 10 ml of tetrahydrofuran was added, and the whole was stirred for 1 hour. Further, 20 ml of an aqueous ammonium chloride saturated solution was gradually added at the same temperature, the whole was heated to a room temperature, and then diethyl ether was added. The organic layer was washed with an aqueous sodium chloride saturated solution, and dried over magnesium sulfate. The solvent was evaporated under a reduced pressure.

The residue was treated by column chromatography wherein silica gel was used. From the effluent of ether/hexane (1:2), 248 mg of transester compound was obtained, and from the effluent of ether/hexane (1:1), 3.82 g (yield: 91%) of the above-mentioned α, β-unsaturated lactone compound (304) was obtained as a colorless oil.

$[\alpha]_D^{29}=+120.9°$ (c=1.12CHCl$_3$).
$^1$H-NMR (CDCl$_3$, δ): 1.98 (3H, s), 2.35 (1H, dd, J=18 Hz, 5.1 Hz), 2.50 (1H, dd, J=18 Hz, 12 Hz), 3.69 (2H, d, J=4.6 Hz), 4.40–4.75 (1H, m), 5.80 (1H, brs), 7.34 (5H, s).

IR ν$_{max}$ (neat) cm$^{-1}$: 1720, 1255, 1122.
MS m/e: 232 (M$^+$), 111 (100%).
Elementary analysis: Calculated (C$_{14}$H$_{16}$O$_3$): C=72.38, H=6.95 Found: C=72.52, H=7.14.

EXAMPLE 20

Preparation of (2S, 3S, 5R)-5-benzyloxymethyl-2,3-epoxy-3-methyl-δ-valerolactone

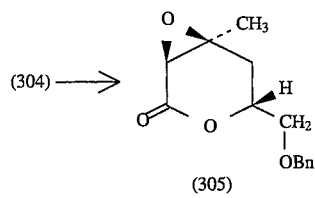

To a solution of 1.0 g (4.31 mmol) of the α, β-unsaturated lactone compound (304) prepared in Example 19 in 5.0 ml of methyl alcohol, 1.47 ml (12.9 mmol) of an aqueous peroxide solution (30%) and then 1.0 ml of 6N-sodium hydroxide aqueous solution was added dropwise, in a water bath (20° C.), and the whole was vigorously stirred. When the above aqueous solutions were added dropwise, gases were vigorously generated. After the stirring was carried out for 40 minutes, the reaction solution was cooled with an ice, and a concentrated hydrochloric acid was carefully added thereto. After adjusting the pH value to 1–2, extraction was carried out with 100 ml of ethyl acetate. The organic layer was washed with 20 ml of an aqueous sodium chloride saturated solution, and dried over magnesium sulfate. The solvent was evaporated under a reduced pressure.

The residue was treated by column chromatography wherein 40 g of silica gel was used. From the effluent of diethyl ether/n-hexane (1:2), 748 mg (yield: 70%) of the above-mentioned α, β-epoxylactone compound (305) was obtained as a colorless oil.

$[\alpha]_D^{29}=-21.9°$ (c=1.02, CHCl$_3$).
$^1$H-NMR (CDCl$_3$, δ): 1.52 (3H, s), 2.20 (2H, d, J=7.8 Hz), 3.48 (1H, s), 3.60 (2H, dd, J=3.9 Hz, 1.2 Hz), 4.56 (2H, s), 4.50–4.80 (1H, m), 7.33 (5H, s).
IR ν$_{max}$ (neat) cm$^{-1}$: 1740, 1290, 1270.
MS m/e: 248 (M$^+$), 91 (100%).

EXAMPLE 21

Preparation of (3S, 5R)-5-benzyloxymethyl-3-hydroxy-3-methyl-δ-valerolactone

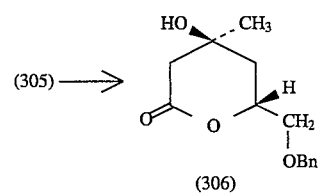

To a suspension of 1.98 g (6.35 mmol) of diphenyl diselenide [C$_6$H$_5$SeSeC$_6$H$_5$] in 6 ml of ethanol, 482 mg (6.35 mmol) of sodium boron hydride was gradually added at a room temperature while paying attention to blowing and heat generation. After stirring for 2 hours, 0.12 ml (2.11 mmol) of acetic acid was added to the resulting orange solution, and the whole was further stirred. Then, 4 ml of a solution of the α, β-epoxylactone compound (305) prepared in Example 20 in ethyl alcohol was added dropwise by a cannula, and the whole was further stirred at a room temperature for 20 minutes.

The resulting solution was diluted with 20 ml of ethyl acetate, and 10 ml of an aqueous sodium chloride saturated solution was added. After stirring at the same temperature for 30 minutes, concentrates hydrochloric acid was added dropwise to adjust the pH value to 1–2 while cooling with an ice. The extraction was carried out with ethyl acetate. The organic layer was dried over anhydrous magnesium sulfate. The solvent was evaporated under a reduced pressure.

The residue was dissolved in 20 ml of toluene. To the resulting solution, 54 mg of pyridinium p-toluenesulfonate was added. After Dean-Stark apparatus was attached, the whole was heated for 30 minutes under reflux. The reaction mixture was cooled with an air, and diluted with 100 ml of diethyl ether. The organic layer was washed with an aqueous sodium bicarbonate saturated solution (20 ml×2) and then with an aqueous sodium chloride saturated solution (20 ml), and dried over an anhydrous magnesium sulfate.

After the solvent was evaporated under a reduced pressure, the residue was treated by column chromatography wherein 50 g of silica gel was used. From the effluent of diethyl ether, 952 mg (yield: 90%) of the above-mentioned hydroxylactone compound (306) was obtained as a colorless oil.

$[\alpha]_D^{28} = -3.28°$ (c=1.02, CHCl$_3$).
$^1$H-NMR (CDCl$_3$, δ): 1.37 (3H, s), 1.87 (2H, dd, J=6.8 Hz, 1.5 Hz), 2.22 (1H, brs), 2.30–2.80 (2H, m), 3.65 (2H, ddd, J=10.7 Hz, 3.9 Hz, 1.5 Hz), 4.57 (2H, s), 4.70–5.00 (1H, m, 7 lines), 7.33 (5H, s).
IR $\nu_{max}$ (neat) cm$^{-1}$: 3450, 1720.
MS m/e: 250 (M$^+$), 91 (100%).

EXAMPLE 22

Preparation of (3S, 5R)-3-hydroxy-5-hydroxymethyl-3-methyl-δ-valerolactone

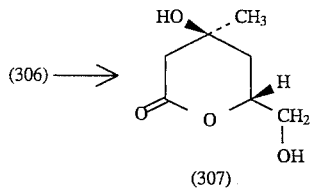

(307)

To a solution of 260 mg (1.05 mmol) of the benzyl ether compound (306) prepared in Example 21 in 5 ml of methyl alcohol, 15 ml of 20% palladium (II) hydroxide-carbon was added, and the whole was stirred in an atmosphere of a hydrogen stream (1 atm.) at a room temperature for 18 hours. After the catalyst was filtered off with celite, the solvent was evaporated under a reduced pressure. The residue was treated by column chromatography wherein 8 g of silica gel was used. From the effluent of ethyl acetate, 163 mg (yield: 97%) of the above-mentioned diol compound (307) was obtained as a colorless gum.

$[\alpha]_D^{28} = +3.54°$ (c=1.13, methyl alcohol).
$^1$H-NMR (CDCl$_3$, δ): 1.48 (3H, s), 1.60–1.95 (3H, m), 2.55 (2H, d, J=6.3 Hz), 2.65 (1H, brs), 3.40–3.70 (2H, brm), 4.55–4.90 (1H, brm).
IR $\nu_{max}$ (neat) cm$^{-1}$: 3400 1730.
MS m/e: 161 (M$^+$), 87 (100%).

EXAMPLE 23

Preparation of (3S, 5R)-6-benzyloxy-3,5-dihydroxy-3-methylhexanol

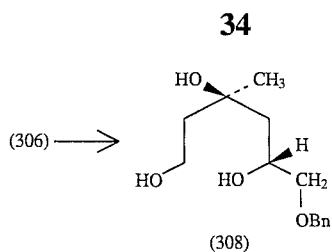

To a solution of 430 mg (1.72 mmol) of hydroxylactone (306) prepared in Example 21 in 8 ml of tetrahydrofuran, 131 mg (3.44 mmol) of lithium aluminum hydride was added while cooling with an ice, and the whole was stirred at a room temperature for 5 hours. An aqueous ammonia saturated solution was carefully added. After stirring, the filtration was carried out, by celite, and the filtrate was concentrated under a reduced pressure.

The residue was treated by column chromatography wherein 20 g of silica gel was used. From the effluent of 5% methyl alcohol/diethyl ether, 405 mg (yield: 93%) of the above-mentioned triol compound (308) was obtained.

$[\alpha]_D^{27} = +8.44°$ (c=1.09, methyl alcohol).
$^1$H-NMR (CDCl$_3$+D$_2$O, δ): 1.30 (3H, s), 1.45–2.00 (4H, m), 3.37 ( 2H, d, J=5.9 Hz ), 3.82 (2H, t, J=5.6 Hz), 4.10–4.40 (1H, m), 4.54 (2H, s) 7.32 (5H, s).
IR $\nu_{max}$ (neat) cm$^{-1}$: 3350, 1120, 860.
MS m/e: 255 (M$^+$), 91 (100%).

EXAMPLE 24

(1) Preparation of (S)-mevalonoactone

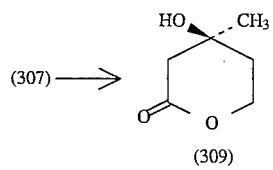

To a solution of 160 mg (1.00 mmol) of diol-lactone compound (307) prepared in Example 22 in 2 ml of tetrahydrofuran, 2 ml of 20% aqueous sodium hydroxide solution was added at a room temperature, and the whole was stirred for 20 minutes. After confirming that the pH value was adjusted to 8–9 by bubbling carbon dioxide gas while cooling with an ice, 235 mg (1.1 mmol) of sodium periodate was added, and the whole was stirred for 30 minutes. After confirming by thin layer chromatography that the starting material disappeared, sodium boron hydride was gradually added, and the whole was stirred. Then, concentrated hydrochloric acid was carefully added at the same temperature (cooling with an ice), the pH value was adjusted to 1–2. The liberated iodines (I$_2$) were reduced with an aqueous sodium thiosulfate saturated solution.

After the extraction was carried out with trichloromethane, the organic layer was dried over anhydrous magnesium sulfate. The solvent was evaporated under a reduced pressure.

The residue was treated by column chromatography wherein 10 g of silica gel was used. From the effluent of diethyl ether, 120 mg of the above-mentioned (S)-lactone compound (309) was obtained.

(2) Preparation of (R)-mevalonolactone

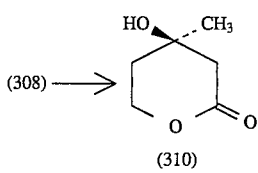

(308) →

(310)

To a solution of 400 mg (1.57 mmol) of the triol compound (308) prepared in Example 23 in 5 ml of methyl alcohol, 20 mg of 20% palladium (II) hydroxide-carbon was added, and the whole was stirred in an atmosphere of a hydrogen stream (1 atm.) at a room temperature for 12 hours. After removing the catalysts by celite, the solvent was evaporated under a reduced pressure to obtain 250 mg of the crude tetraol compound.

The crude tetraol compound was dissolved in 2 ml of $H_2O$. To the solution, an aqueous periodic acid solution [prepared by dissolving 394 mg (1.73 mmol) of $HIO_4\text{-}2H_2O$ in 2 ml of $H_2O$] was added dropwise, and the whole was stirred at the same temperature for 5 minutes. The completion of the reaction, i.e., the conversion of the diol-aldehyde compound (311):

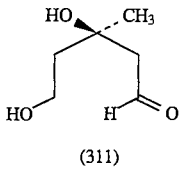

(311)

to the lactol compound (312):

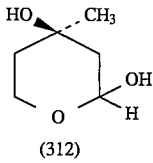

(312)

was confirmed by thin layer chromatography. Then, 5 ml of concentrated sulfuric acid was added to the reaction solution. After 1.05 g (10.5 mmol) of anhydrous chromium (VI) oxide was added to the reaction solution, the whole was stirred for 30 minutes. Then, the neutralization was carried out by adding powdery sodium bicarbonate, and the extraction was carried out with trichloromethane. The organic layer was dried over anhydrous magnesium sulfate, and the solvent was evaporated under a reduced pressure. The residue was treated by column chromatography wherein 10 g of silica gel was used. From the effluent of diethyl ether, 162 mg (yield: 79%) of the above-mentioned (R)-lactone compound (310) was obtained. The physicochemical data of the (R)- and (S)-mevalonolactones are as follows:

$^1$H-NMR (CDCl$_3$, δ): 1.395 (3H, s), 1.90 (2H, dd, J=5.1 Hz, 4.4 Hz ), 2.47 ( 1H, d, J=17.3 Hz ), 2.71 ( 1H, d, J=17.3 Hz), 2.50 (1H, brs), 3.20–3.80 (2H, m).

IR $ν_{max}$ (neat) cm$^{-1}$: 3400, 1710, 1260.

(S)-form (309):

$[α]_D^{27}$=−22.3° (c=1.07, ethyl alcohol).

(R)-form (310):

$[α]_D^{28}$=−21.5° (c=1.10, ethyl alcohol).

Although the present invention has been described with reference to specific embodiments, various changes and modifications obvious to those skilled in the art are deemed to be within the spirit, scope and concept of the invention.

We claim:

1. An optically active valerolactone compound of the general formula (31):

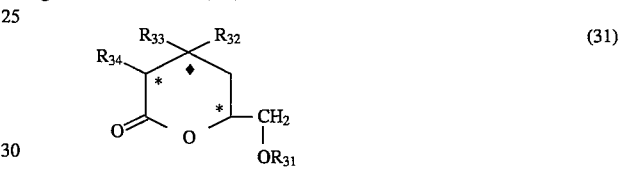

wherein $R_{31}$ represents a hydrogen atom or a group for protecting a hydroxy group, $R_{32}$ represents a vinyl, ethynyl or phenyl group, $R_{33}$ is a hydroxy group, and $R_{34}$ is a hydrogen atom, and the chiral central carbon atoms marked with symbols * and ♦ in said formula (31) alternatively have one of an R-configuration or an S-configuration.

2. The valerolactone compound of claim 1 wherein $R_{32}$ represents a vinyl group.

3. The valerolactone compound of claim 1 wherein $R_{32}$ represents an ethynyl group.

4. The valerolactone compound of claim 1 wherein $R_{32}$ represents a phenyl group.

* * * * *